United States Patent [19]

Weber et al.

[11] Patent Number: 5,710,252

[45] Date of Patent: Jan. 20, 1998

[54] METHOD FOR RECOMBINANT YEAST EXPRESSION AND ISOLATION OF WATER-SOLUBLE COLLAGEN-TYPE POLYPEPTIDES

[75] Inventors: Shane Crawford Weber, Woodbridge, Conn.; Arthur Herman Herz, Rochester, N.Y.

[73] Assignee: Eastman Kodak Company, Rochester, N.Y.

[21] Appl. No.: 383,748

[22] Filed: Feb. 3, 1995

[51] Int. Cl.⁶ .................................................. A61K 38/39
[52] U.S. Cl. ..................... 530/356; 530/412; 435/69.1
[58] Field of Search ........................ 530/356, 412; 435/69.1

[56] References Cited

U.S. PATENT DOCUMENTS

| | | | |
|---|---|---|---|
| 3,314,861 | 4/1967 | Fujii | 530/356 |
| 4,826,765 | 5/1989 | Greene et al. | 435/68 |
| 5,114,840 | 5/1992 | Tryggvason et al. | 435/6 |
| 5,212,074 | 5/1993 | Kiefer et al. | 435/69.6 |
| 5,217,891 | 6/1993 | Brake et al. | 435/226 |
| 5,235,041 | 8/1993 | Cappello et al. | 530/353 |
| 5,243,038 | 9/1993 | Ferrari et al. | 536/23.1 |
| 5,496,712 | 3/1996 | Cappello et al. | 435/69.1 |

FOREIGN PATENT DOCUMENTS

| | | |
|---|---|---|
| 285675 | 10/1988 | European Pat. Off. . |
| 2685347 | 6/1993 | France . |
| 03533 | 5/1988 | WIPO . |
| 05177 | 5/1990 | WIPO . |
| 09695 | 6/1992 | WIPO . |
| 10567 | 6/1992 | WIPO . |

OTHER PUBLICATIONS

Englard et al., 182 Meth. Enz. 285–300 (Deutscher, ed. 1990).

Kennedy, 182 Meth. Enz. 339–43 (Deutscher, ed. 1990).

Tirrell et al, *MRS Bulletin I*, XVI (7), pp. 23–28, 1991.

Goldberg et al, *Gene*, 80, pp. 305–314, 1989.

Futuretech® Briefing No. 78, Mar. 27, 1989.

*Primary Examiner*—Rebecca E. Prouty
*Assistant Examiner*—Enrique D. Longton
*Attorney, Agent, or Firm*—J. Lanny Tucker

[57] ABSTRACT

A method for preparing and purifying collagen-type polypeptides (or biopolymers) has been developed. The polypeptides are prepared by recombinant DNA technology using yeast host cells. Once expressed in the host cell culture, the polypeptide is purified by a series of centrifugations, isoprecipitation, ion exchange (or other chromatography), and diafiltration steps. Treatments with a protease and a calcium salt are also carried out at some point. It is also desirable to diafilter the purified fractions from the last chromatography to exchange ions which make the resulting polypeptide more compatible with its intended use.

22 Claims, 5 Drawing Sheets

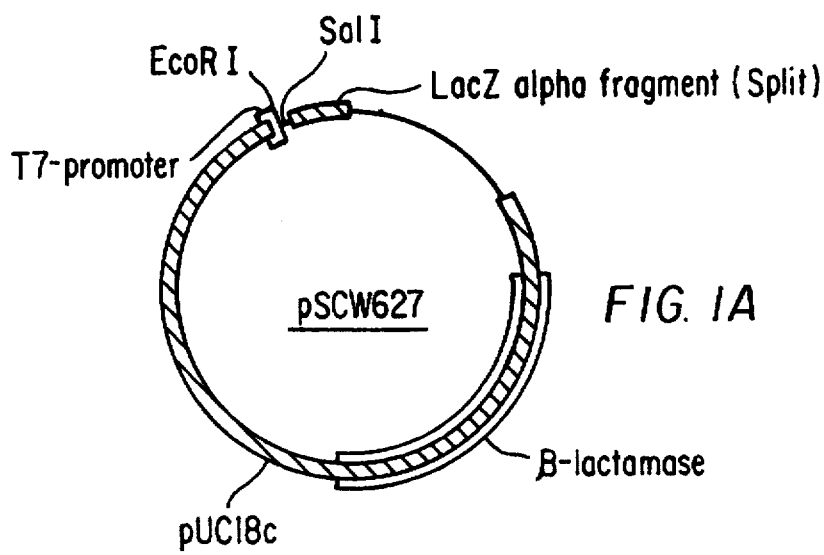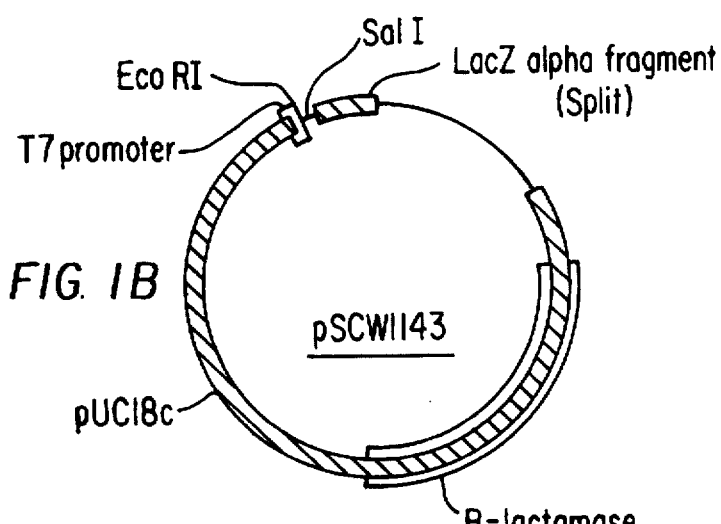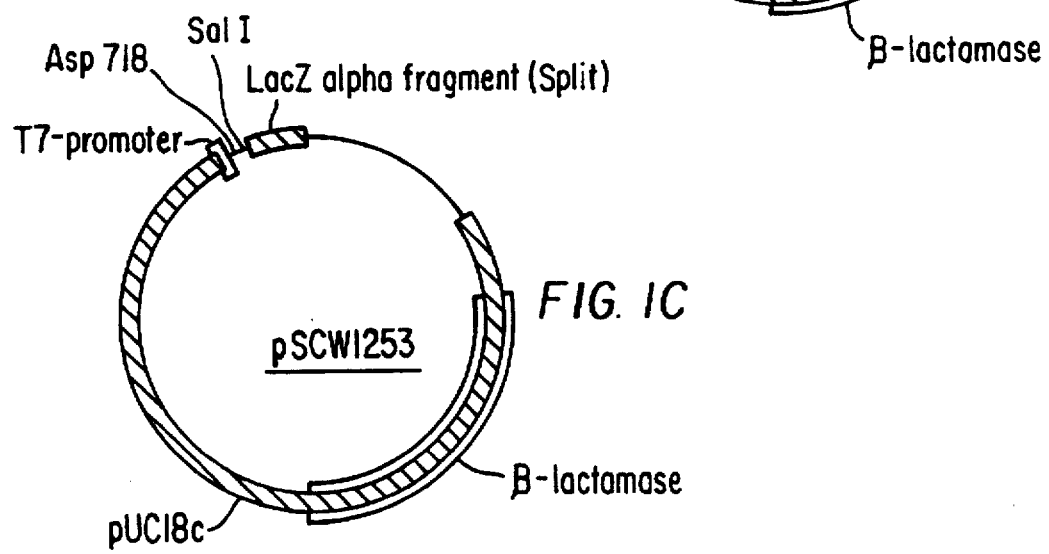

METHOD FOR RECOMBINANT YEAST EXPRESSION AND ISOLATION OF WATER-SOLUBLE COLLAGEN-TYPE POLYPEPTIDES

FIELD OF THE INVENTION

The present invention relates to the use of recombinant DNA technology and a combination of purification techniques to obtain useful collagen-type polypeptides. In particular, it relates to a method for recombinant expression of collagen-type polypeptides in yeast host cells, and includes the isolation of the expressed polypeptides.

BACKGROUND OF THE INVENTION

Recombinant DNA technology has been applied to the isolation of natural genes and the expression of those genes in various host cells. In addition, it has been used to produce modified proteins using modified genes, or combinations of portions of natural genes. Briefly, such procedures include: (1) isolation and purification (or chemical synthesis) of a specific gene or gene segment containing the genetically coded information for the amino acid sequence of the desired protein or polypeptide, (2) recombination of the gene segment with an appropriate transfer vector, and (3) transfer of the modified vector to the appropriate host cell for expression of the protein or polypeptide.

With the advent of efficient and automated methods for chemical synthesis of DNA, it has become possible to synthesize entire genes and to modify them during synthesis. Most of these attempts have been directed to the production of natural or modified versions of the natural polypeptides. Less attempts have been made to use the technology to produce entirely new polypeptides.

Beginning in the early 1980's, however, researchers began publishing and patenting new approaches to the use of recombinant technology to product new proteins, or "biopolymers" as they are conventionally known. Many genes have been cloned and expressed from plasmid vectors for production of enzymes, antibodies and other proteins which have various physiological functions. Yet, fewer genes have been cloned that code for all or part of structural proteins such as components of the extracellular matrix in multicellular higher organisms. Such proteins are the subject of growing interest, and include collagens, elastin, fibrinectin and other fibrous proteins.

Some early work to produce structural proteins is described in U.S. Pat. No. 5,243,038 (Ferrari et al) relating to high molecular weight recombinant polypeptides having repetitive oligomeric units. Some of the described proteins have the same composition and physical properties of certain silks and were produced using *Escherichia coli* host cells.

Various researchers, such as Tirrell et al [*MRS Bulletin*, XVI(7), 22-28, 1991], have described their efforts to make polymeric materials using recombinant DNA techniques, as well as the considerable problems that must be overcome for success in this field of work.

Certain small (100 amino acid) collagen-like biopolymers (containing repeating glycine-proline-proline amino acids) are described in U.S. Pat. No. 5,089,406 (Williams et al), but the described materials are genetically unstable because of recombination of the DNA into altered sequences.

WO-A-90/05177 (published May 17, 1990) describes the synthesis of synthetic proteins which have properties similar to silk, elastin, keratin and collagen from *E. coli*. The proteins have various components which provide various functions in a given environment.

Other synthetic structural proteins are described in WO-A-92/09695 (published Jun. 11, 1992), and collagen-like materials were produced by Goldberg et al (*Gene*, 80, 305-314, 1989) using *E. coli*. Goldberg et al noted (Page 310) that the polypeptide they produced within the cell degraded (80%) in only 40 minutes under modest heat (41° C.).

FR-A-2,685,347 (published Jun. 26, 1993) describes the preparation of recombinant peptides as substitutes for gelatin having diverse uses. The described peptides are considered similar to type I bovine collagen, were prepared using *E. coli* host cells, and are alleged to represent an improvement in homogeneity for their use in holography. The specific peptides contain many triplets of the amino acids glycine-proline-alanine alternating with triplets of the amino acids glycine-glutamic acid-arginine. Histidine triplets are specifically included in the peptides to provide affinity for a nickel-NTA-agarose recovery resin, and methionine is included between the histidine triplets and other non-histidine triplets to permit chemical degradation so that only the noted triplets are retained in the final product. A cysteine is included for binding to chromatographic resins or proteins, and a leucine is placed critically between the methionine and histidine because of its restriction site. Thus, the polypeptides have a complicated sequence of amino acids, particularly on one end, for capture and recovery of the desired material. There is no indication that the described process was used to produce anything but very small amounts (laboratory scale) of the polypeptides, nor is there any indication of a purification technique to provide highly pure product. The actual usefulness of the described materials is not demonstrated in the noted publication.

The foregoing procedures using *E. coli* host cells are the conventional procedures because of the ease with which that bacterium can be used in recombinant technology. It is a well known and characterized microorganism.

In contrast, yeast cells are less well known. It is unpredictable whether a given yeast host cell will accurately express a given polypeptide especially a repetitive biopolymer since repetitive DNA is widely thought to be recombigenic, that is likely to rearrange into altered perturbations of the original sequences.

The use of *E. coli* as host cell has a number of disadvantages. Repetitive biopolymers prepared therein are known to be recombigenic. Moreover, *E. coli* cells do not usually secrete proteins effectively into the extracellular medium, and the expression level is usually low (less than 100 mg/l), requiring lengthy, tedious purification procedures from cell paste lysates. Also, proteins thus secreted may be contaminated with enterotoxins, requiring further purification before they can be safely used for human needs.

There remains a need for an effective and efficient means for producing and isolating collagen-type polypeptides using recombinant DNA techniques. Moreover, it would be highly desirable to be able to produce large quantities of collagen-type polypeptides in a reproducible manner.

SUMMARY OF THE INVENTION

The present invention overcomes the noted problems and provides a significant advance in the art by providing a method for preparing and isolating a recombinant water-soluble collagen-type polypeptide comprising the steps of:

A) preparing and expressing a water-soluble collagen-type polypeptide in a yeast host cell culture using recombinant DNA technology, B) after centrifugation or diafiltration of the culture, isolating the expressed water-soluble collagen-type polypeptide by isoprecipitation at a pH which is within ±2 pH units of the isoelectric point of the collagen-type polypeptide, C) after centrifugation of the supernatant obtained in step B, resuspending the resulting pellet in a buffer, D) after centrifugation of the buffered solution formed in step C, subjecting the supernatant thereby obtained to ion exchange chromatography to capture the collagen-type polypeptide, E) obtaining at least one elution fraction and subjecting it to either hydrophobic interaction chromatography or a second ion exchange chromatography, and F) recovering the water-soluble collagen-type polypeptide from at least one elution fraction obtained in step E, wherein between steps B and E, treating the collagen-type polypeptide, independently, with a calcium salt and a protease.

The method of the present invention provides polypeptides which are useful in a variety of applications. The preparatory method uses recombinant technology to produce polypeptides in a reproducible manner, and in larger quantities than normally obtained with conventional techniques. These advantages are achieved by the use of yeast host cells and a specific combination of steps and conditions for isolating the expressed polypeptides.

It was surprising that yeast cells were useful as host cells in the practice of the present invention because repetitive DNA is widely believed to be recombigenic, that is, subject to rearranging to altered perturbations of the original sequence. Yet, that does not occur in the case of the polypeptides expressed in yeast host cells, particularly baker's yeast, or *Saccharomyces cerevisiae*. Yeast host cells also provided secreted polypeptides which are not contaminated with enterotoxins and which are stable in the extra-cellular medium. Because yeast host cells are relatively inexpensive, the present invention can be readily scaled to industrial production.

BRIEF DESCRIPTION OF THE DRAWINGS

FIGS. 1A, 1B and 1C are a schematic diagram of cloning plasmids which can be used in the recombinant preparation of a collagen-type polypeptide, as described in Example 1 below.

DETAILED DESCRIPTION OF THE INVENTION

Figure 2A:
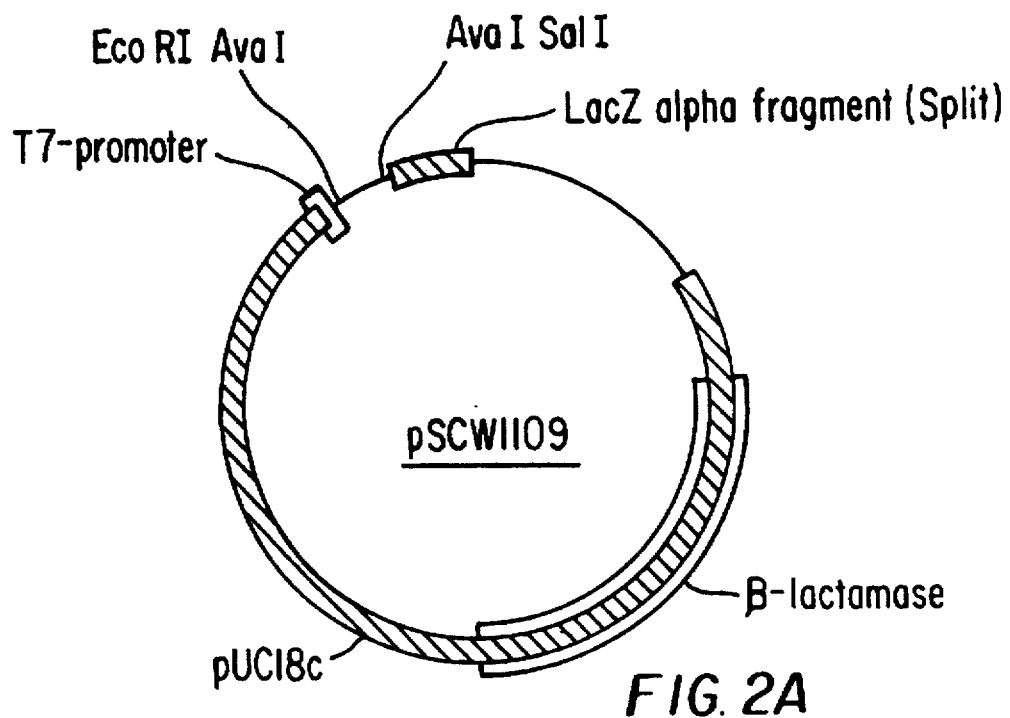
FIGS. 2A and 2B are a schematic diagram of certain "monomer plasmids" used in the recombinant preparation of a collagen-type polypeptide, as described in Example 1 below.

The polypeptides, biopolymers or nucleic acids described herein and prepared by this invention are not known to occur in nature in an isolated state.

The term "polypeptide" is used herein to refer to sequences having at least 20 amino acids, such sequences having at least one occurrence of one or more of the peptide sequences identified herein as formulae I, II and III, or a tripeptide contained in these three peptide sequences.

The terms "biopolymer" and "protein" are used interchangeably and are meant to refer to molecules having more amino acids than the specific polypeptides described herein, but including at least one of those polypeptides.

Amino acids are described herein by the conventional three-letter symbol and nucleotides are identified using the conventional single-letter symbols for the bases.

The polypeptides prepared by the method of this invention have a variety of uses. One preferred use is a peptizer to control the nucleation and growth of silver halide grains. A demonstration of such utility is shown in copending and commonly assigned U.S. Ser. No. 08/383,348, filed on even date herewith by Keevert, Jr., Weber, Jagannathan and Klein and entitled SILVER HALIDE EMULSIONS, ELEMENTS AND METHODS OF MAKING SAME USING SYNTHETIC BIOPOLYMER PEPTIZERS.

However, the biopolymers have other potential uses as biosensors, binders for drug delivery systems, non-allergenic materials for human plastic surgery, linear electron accelerating conducting wires for what are known as "biochips" (see for example, U.S. Pat. No. 4,764,415), as core structure elements for organizing dyes three dimensionally for non-linear optic elements, as uranium salt recovery materials, and as peptide food additives.

Particular polypeptides prepared by the method of this invention have one of the following peptide sequences represented as formulae I, II or III:

I:
{[(Gly Pro Gln) (Gly Pro Glu)$_4$]$_2$}$_n$

II:
Gly Pro Glu{[(Gly Pro Gln) (Gly Pro Glu)$_4$]$_2$}$_n$

III:
Gly Pro Xaa$_1$ Gly Leu Xaa$_2$ Gly Pro Arg Gly Pro Pro
Gly Ala Ser Gly Ala Pro Gly Pro Glu Gly Phe Gln Gly wherein Xaa$_1$ and Xaa$_2$ are independently the amino acids identified as Met, Ile, His, Lys, Asn, Tyr or Gln, and n is 1 to 25.

Further details about such polypeptides are provided in copending and commonly assigned U.S. Ser. No. 08/383, 804, filed on even date herewith by Weber and McElver and entitled COLLAGEN-LIKE PEPTIDE SEQUENCES, BIOPOLYMERS CONTAINING SAME, NUCLEIC ACIDS ENCODING SAME, VECTORS AND HOST CELLS CONTAINING SAME.

Representative examples of such polypeptides include:

SEQ ID NO:1:
  Gly Pro Glu {[(Gly Pro Gln) (Gly Pro Glu)$_4$]$_2$}$_3$
SEQ ID NO:2:
  Gly Pro Glu {[(Gly Pro Gln) (Gly Pro Glu)$_4$]$_2$}$_4$
SEQ ID NO:3:
  Gly Pro Glu {[(Gly Pro Gln) (Gly Pro Glu)$_4$]$_2$}$_9$
SEQ ID NO:4:
  {[(Gly Pro Gln) (Gly Pro Glu)$_4$]$_2$}$_1$
SEQ ID NO:5:
  {[(Gly Pro Gln)(Gly Pro Glu)$_4$]$_2$}$_{18}$
SEQ ID NO:6:
  Gly Pro Ile Gly Leu Ile Gly Pro Arg Gly Pro Pro
  Gly Ala Ser Gly Ala Pro Gly Pro Glu Gly Phe Gln
  Gly
SEQ ID NO:7:
  Gly Pro Lys Gly Leu Lys Gly Pro Arg Gly Pro Pro

-continued

```
        Gly Ala Ser Gly Ala Pro Gly Pro Glu Gly Phe Gln
        Gly
SEQ ID NO:8:
        Gly Pro Asn Gly Leu Asn Gly Pro Arg Gly Pro Pro
        Gly Ala Ser Gly Ala Pro Gly Pro Glu Gly Phe Gln
        Gly
SEQ ID NO:9:
        Gly Pro Tyr Gly Leu Tyr Gly Pro Arg Gly Pro Pro
        Gly Ala Ser Gly Ala Pro Gly Pro Glu Gly Phe Gln
        Gly
SEQ ID NO:10:
        Gly Pro Gln Gly Leu Gln Gly Pro Arg Gly Pro Pro
        Gly Ala Ser Gly Ala Pro Gly Pro Glu Gly Phe Gln
        Gly
SEQ ID NO:11:
        Gly Pro Met Gly Leu Met Gly Pro Arg Gly Pro Pro
        Gly Ala Ser Gly Ala Pro Gly Pro Glu Gly Phe Gln
        Gly
SEQ ID NO:12:
        Gly Pro His Gly Leu His Gly Pro Arg Gly Pro Pro
        Gly Ala Ser Gly Ala Pro Gly Pro Glu Gly Phe Gln
        Gly
SEQ ID NO:13:
        Gly Pro Ile Gly Leu Met Gly Pro Arg Gly Pro Pro
        Gly Ala Ser Gly Ala Pro Gly Pro Glu Gly Phe Gln
        Gly
SEQ ID NO:14:
        Gly Pro Met Gly Leu Ile Gly Pro Arg Gly Pro Pro
        Gly Ala Ser Gly Ala Pro Gly Pro Glu Gly Phe Gln
        Gly
SEQ ID NO:15:
        {[(Gly Pro Gln) (Gly Pro Glu)$_4$]$_2$}$_9$
and
SEQ ID NO:16:
        Gly Pro Glu {[(Gly Pro Gln) (Gly Pro Glu)$_4$]$_2$}$_{18}$
```

The method of this invention to prepare the noted biopolymers can use conventional DNA recombinant techniques (consider, for example, *Recombinant DNA*, 2nd Ed., W. H. Freeman, Inc., 1992, *Molecular Cloning: A Laboratory Manual*, 2nd Ed., Vols. I, II and III, Cold Spring Harbor Press, 1989, *Guide to Molecular Cloning Techniques, Methods in Enzymology*, Vol. 152, Academic Press, Inc., 1987, *Guide to Yeast Genetics and Molecular Biology, Methods in Enzymology*, Vol. 194, Academic Press, Inc., 1991 among many other well known textbooks and journal publications). Conventional protein expression procedures using various yeast host cells can be practiced. The host cells typically contain a recombinant vector which comprises the nucleic acid of interest operationally linked to nucleic acid sequences which allow expression of the desired nucleic acid in the host cells.

A more specific preparation includes the use of a yeast host cell (for example, baker's yeast or *Saccharomyces cerevisiae*) for polypeptide expression, in the presence or absence of an N-terminus eight amino acid epitope (identified as the FLAG™ epitope, owned by Immunex Corp. and described more fully by Hopp et al, *Biotechnology*, 6, 1204–1210, 1988) and several additional amino acids including a site for proteolytic cleavage removal at a particular lysine.

The general method of this invention includes the following steps and conditions:

Step A

Expression of the water-soluble collagen-type polypeptides is carried out in a yeast host cell culture using recombinant DNA technology. The various recombinant procedures are well known and are described in detail in Example 1 below. In a preferred embodiment, expression is carried out in the presence of at least about 10 mmol/l of calcium ion. Preferably, at least from about 20 to about 30 mmol/l of calcium ion is used to improve polypeptide expression. The source of calcium ion can be any useful calcium salt which does not interfere in any manner with the expression process. For example, calcium chloride, calcium sulfate or calcium nitrate can be used.

Step B

The cell culture is centrifuged or diafiltered to remove the yeast cells. The expressed polypeptide is in the supernatant. Centrifugation can be carried out using any suitable equipment and time. For example, the cell culture can be centrifuged at 10,000g for up to 60 minutes (preferably, about 10 minutes).

Alternatively or in addition to the centrifugation, the supernatant can be diafiltered using suitable conventional equipment. For example, it can be filter sterilized using a conventional 1,000,000 molecular weight cutoff Filtron tangential flow filtration unit. Preferably, when diafiltration is used, it is carried out subsequent to centrifugation.

The supernatant from these separation techniques is then subjected to isoprecipitation at a pH which is within ±2 pH units of the isoelectric point of the expressed polypeptide. Preferably, isoprecipitation is carried out within ±1 pH unit of the isoelectric point. By having the pH so close to the polypeptide isoelectric point, the polypeptide preferentially precipitates over other materials in the supernatant. Usually, precipitation is carried out for several hours at a temperature of less than about 25° C.

The isoelectric point is defined as the pH where the positive and negative charges in the polypeptide molecule are equal. Various methods are known for measuring the isoelectric point, and it is known that this parameter will vary with the polypeptide composition, and solution ionic strength (see Cohen et al, "Applied Chemistry at Protein Interfaces" in *Advances in Chemistry Series*, No. 145, Am.Chem.Soc., Washington, D.C., 1975, pages 198–217). Because polypeptides are least soluble at their isoelectric points, at that pH, they generally precipitate even without salting out procedures.

Preferably, the pH of the isoprecipitation procedure is controlled without the need to add "pH control agents", that is bases or acids which adjust the pH. However, in some instances, an acid or alkali may be used to adjust the pH to the desired level. For that purpose, hydrochloric acid and sodium hydroxide are useful pH control agents.

Step C

The supernatant containing the precipitated polypeptide is then centrifuged using standard conditions and equipment to form a pellet of the polypeptide. The supernatant is discarded.

The pellet is resuspended in a suitable buffered solution which can also include various sodium or calcium salts, chelating agents, and microbial static agents. Useful buffers include tris(hydroxymethyl)aminomethane, phosphate, tricine and others which would be readily apparent to one skilled in the art to provide a pH of from about 6 to about 10. More likely, the pH is from about 7 to about 8.5.

Step C1

An optional but preferred subsequent step is to heat the buffered solution prepared in Step C to at least about 45° C. (preferably from about 50° to about 65° C.) for at least 10 minutes (preferably from about 10 to about 25 minutes). This heating causes the polypeptide to have a more linear and monomolecular configuration in solution. It is also preferred that the buffered solution contain a calcium salt (as described below). A protease can be added after heating to degrade unwanted polypeptides or proteins in the solution, and to cleave any unwanted amino acids (such as the FLAG™ epitope amino acid sequence) from the polypeptide of interest. More details of the protease treatment are provided below.

Step D

After another centrifugation step, the supernatant is subjected to a first ion exchange chromatography procedure to purify the polypeptide using any suitable anionic ion exchange column that contains chemical functional groups which are positively charged at the pH of the supernatant applied and buffers used for binding elution, such that the anionic polypeptide is primarily bound electrostatically. The wash buffer contains additional salt at a concentration sufficient to electrostatically elute impurities but not the bound polypeptide. Elution buffer contains additional salt at sufficient concentration to electrostatically elute the bound polypeptide.

Generally, the elution fluids are sodium chloride solutions of varying concentrations. After the supernatant is added to the column, the column is washed several times (at least twice) at appropriate flow rates until the eluant has an absorbence less than 0.001 OD at 214 nm. This indicates that all nonbound materials have been washed through the column.

Generally, one or more elution fractions containing the polypeptide of interest are pooled and treated further.

Step D1

Optionally, the fraction can be heated a first or second time to make the polypeptide configuration more linear. The heating conditions are described above in Step C1. It is also possible to treat the fraction with a calcium salt or protease (to form a proteolytic solution) at this time, in place of Step C1 noted above.

Step D2

A calcium chelating agent, such as ethylenediaaminetetraacetic acid, can also be added at this time to complex with calcium ions.

Step E

The elution fraction described above is then subjected to either a second ion exchange chromatography or to what is known as hydrophobic interaction chromatography.

If a second ion exchange chromatography is carried out, it is similar to that described above in Step D.

Alternatively, hydrophobic interaction chromatography can be carried out to further purify the polypeptide in the presence of salts at suitable concentrations based on hydrophobic binding interaction between the polypeptide and suitable hydrophobic groups on the column matrix.

A hydrophobic chromatographic column contains suitable chemical functional groups that are hydrophobic in nature such as $C_8$ or $C_{18}$ aliphatic or phenyl ring moieties. The eluant fraction containing the polypeptide from an anionic ion exchange column in a salt concentration suitable to cause binding of the polypeptide is applied to the hydrophobic chromatographic column. The wash buffer contains a lower salt concentration such that impurities are eluted but the polypeptide is still retained on the column. The final elution buffer is a salt concentration low enough such that the polypeptide no longer is bound but is removed freely. Phenyl groups are preferred hydrophobic groups, and ammonium sulfate is the preferred salt when using hydrophobic interaction chromatography.

Step E1

Optionally but preferably, one or more elution fractions obtained from Step E are diafiltered to replace the ions present in the solution with different ions that may be more compatible with the intended use of the polypeptide. In a preferred embodiment, the elution fraction ions [typically, tris(hydroxymethyl)aminomethane, phosphate, ammonium, sulfate, calcium and magnesium] which are associated with various buffers, are replaced with ions compatible with photographic silver halide emulsions. Such "new" ions include, but are not limited to, potassium, sodium, nitrate, chloride, or perchlorate. Calcium ion chelating agents can also be used at this time.

Thus, in a preferred embodiment involving the use of polypeptides for silver halide emulsions, molecules and salts [exemplified by tris(hydroxymethyl) aminomethane and ammonium sulfate] which may influence the performance of such emulsions are removed by appropriate ion-exchange procedures, for example, diafiltration, and are then replaced by ions that are compatible with optimum silver halide performance.

In general terms, those compounds and ions should be removed which can (a) oxidize latent image silver [for example, mercury (II)], (b) reduce silver halide [for example Fe(II)] and (c) act as effective silver (I) ligands either in yielding sparingly soluble silver salts (for example, bromide), or in forming soluble silver (I) complexes (for example, amines and thiocyanate ions).

A reason for the avoidance of ligands that produce soluble silver (I) complexes, is that they increase silver halide growth rates and promote formation of storage fog [A. Herz, *Progress in Basic Principles of Imaging Science*, (Proceedings ICPS, Cologne, 1986) F. Granzer and E. Moisar, Eds., F. Vieweg & Sohn, Braunschweig, 1987, pp. 226–227]. Similarly, organic and inorganic ammonium salts (for example, ammonium sulfate) are known to change the stability of photographic emulsion layers (see U.S. Pat. No. 5,232,827 of Lok and Herz).

Hence, when used with silver halide emulsions, it is advantageous to exclude from the polypeptide the noted ions and compounds. They can be replaced by innocuous ions which are compatible with photographic emulsions, preferred among these being alkali ions (such as potassium or sodium), nitrate, perchlorate, sulfate and hydrocarbon sulfonates (such as the benzenesulfonate anion).

Other uses of the polypeptide may require that other different ions be added to the polypeptide solution to replace those removed by diafiltration.

Diafiltration can be carried out using any suitable commercially available equipment that retains macromolecules (usually greater than 10,000 daltons) as large as possible in order to retain the polypeptide while allowing smaller molecules to be removed.

Step F

After dialysis, the purified polypeptide can be recovered and stored in a solution suitable for later use. For example, if the use is as a peptizer for photographic emulsions, the solution should be compatible with such emulsions (for example, a potassium nitrate solution), or preferably freeze dried (Step F1) using conventional procedures and equipment. The resulting dried collagen-type polypeptide may be provided in various forms including, but not limited to, powders, pellets, granules or shredded gel.

In the method just described, the polypeptide can be heated to change its configuration at any time. Thus, the heating is not limited to Steps C1 or D1 as described above. However, the heating conditions are generally those described for Step C1 above.

In addition, the use of a protease or calcium salt described above can be at any point between Step B and E, and is not limited to Steps C1, D1 and D2 described above.

Useful proteases include, but are not limited to, trypsin, chymotrypsin, thermolysin, papain, pepsin, endo Arg C, endo Asp N, endo Glu C and endo Lys C. A skilled worker would be able to determine a useful protease (that is, one that does not degrade the bipolymer), the proper amounts and suitable pH with routine experimentation in view of the considerable information available in the art regarding alternative proteases. A preferred protease is commercially available trypsin. Generally, the protease is used at a pH at which enzyme activity is optimum, such as within ±1 pH unit of the protease optimum activity pH.

Useful calcium salts include, but are not limited to, calcium chloride, calcium nitrate, and calcium sulfate. Useful amounts are equal to or greater than the concentration of carboxyl groups in the polypeptide sample, with from about 10 to about 30 mmol being preferred. Calcium chelating agents are also well known and could be readily chosen by a skilled worker in the art.

A preferred embodiment of this invention is a method for preparing and isolating a recombinant water-soluble collagen-type polypeptide comprising the steps of:

A) preparing and expressing a water-soluble collagen-type polypeptide in a culture of *Saccharomyces cerevisiae* using recombinant DNA technology,
  B) after centrifugation of the culture, isolating the expressed water-soluble collagen-type polypeptide by subjecting the resulting supernatant to isoprecipitation at a pH of from about 3 to about 4,
  C) after centrifugation of the supernatant obtained in step B, resuspending the resulting pellet in a buffered solution of a calcium salt,
  C1) after heating the buffered solution to at least about 45° C. for at least 10 minutes, mixing the solution with a protease to form a proteolytic solution having a pH of from about 7 to about 9,
  D) after centrifugation of the solution, subjecting the supernatant thereby obtained to step gradient ion exchange chromatography to capture the collagen-type polypeptide using buffered solutions of sodium chloride and a DEAE chromatography column,
  E) after heating at least one elution fraction obtained in step D to at least about 45° C. for at least 10 minutes, and subsequently cooling, subjecting the heated and cooled elution fraction to hydrophobic interaction chromatography using ammonium sulfate solutions and a phenyl sepharose chromatography column,
  E1) subjecting at least one elution fraction obtained in step E to diafiltration to replace ions in the elution fraction with different ions,
  F) recovering the collagen-type polypeptide from the resulting diafiltered elution obtained in step E1, and
  F1) vacuum drying the recovered water-soluble collagen-type polypeptide.

Another embodiment includes a method for preparing and isolating a recombinant water-soluble collagen-type polypeptide comprising the steps of:

A) preparing and expressing a water-soluble collagen-type polypeptide in a culture of *Saccharomyces cerevisiae* using recombinant DNA technology,
  B) after centrifugation or diafiltration of the culture, isolating the expressed water-soluble collagen-type polypeptide by subjecting the resulting supernatant to isoprecipitation at a pH of from about 3 to about 4,
  C) after centrifugation of the supernatant obtained in step B, resuspending the resulting pellet in a buffered salt solution, the solution having a pH of from about 7 to about 9,
  D) after centrifugation of the buffered salt solution, subjecting the supernatant thereby obtained to step gradient ion exchange chromatography to capture the collagen-type polypeptide using buffered solutions of sodium chloride and a DEAE chromatography column,
  D1) adding a buffered solution of a calcium salt and a protease to at least one elution fraction obtained in step D to form a proteolytic solution,
  D2) adding a calcium ion chelating agent to the proteolytic solution,
  E) subjecting the proteolytic solution to a second step gradient ion exchange chromatography using sodium chloride solutions and a DMAE chromatography column,
  E1) subjecting at least one elution fraction obtained in step E to diafiltration to replace ions in the elution fraction with different ions,
  F) recovering the collagen-type polypeptide from the resulting diafiltered elution fraction obtained in step E1, and
  F1) vacuum drying the recovered water-soluble collagen-type polypeptide.

More specific details of the preferred embodiment of this invention are described in Example 2 below. Example 1 shows details of a second useful embodiment of this invention.

The following examples are included to illustrate the practice of this invention, and are not to be used to limit its scope. All percentages are by weight, unless otherwise indicated.

EXAMPLE 1

Recombinant DNA Preparation and Purification of Biopolymer

This example demonstrates a preferred method for preparing a biopolymer of this invention. Specifically, it illustrates the use of *Saccharomyces cerevisiae* (*S. cerevisiae*) as the host organism to prepare the polypeptide (or biopolymer) identified herein as SEQ ID NO:3. This biopolymer comprises the amino acid sequence "Gly Pro Glu" followed by 9 replicates of the polypeptide sequence SEQ ID NO:4, also identified herein as the "GG monomer".

To prepare a double strand nucleic acid that encodes the GG monomer, a sequence with optimum codon usage for *S. cerevisiae* was chosen. Two complementary DNA oligonucleotides encoding the GG monomer were chemically synthesized by standard automated trityl phosphoamidate reactions (F. Eckstein, *Oligonucleotide and Analogs*, Oxford University Press, Oxford, England, 1991). The top strand was the encoding strand. Additional sequences needed for cloning of the hybridized oligonucleotides and the directional assembly of the DNA fragments into DNA concatenated polymers that code for biopolymers are also included in these oligonucleotides (as described below).

The top strand oligonucleotide had the sequence:

SEQ ID NO:17:
5'- AATTCGGTCC CGAGGGTCCA CAAGGTCCAG AAGGTCCAGA
AGGTCCAGAA GGTCCAGAAG GTCCACAAGG TCCAGAAGGT CCAGAAGGTC
CAGAAGGTCC CGAGCTAAG-3'

The complementary bottom strand oligonucleotide had the sequence:

SEQ ID NO:18:
5'- TCGACTTAGC TCGGGACCTT CTGGACCTTC TGGACCTTCT
GGACCTTGTG GACCTTCTGG ACCTTCTGGA CCTTCTGGAC CTTCTGGACC
TTGTGGACCC TCGGGACCG-3'

Inside the ends of these two oligonucleotides were encoded Ava I nonpalindromic restriction sites (underlined in SEQ ID NO:17) which, upon proper manipulation, oriented the directional assembly of DNA fragments into repeated head-to-tail DNA concatamers, encoding repeated biopolymers. For SEQ ID NO:3 biopolymer, the form of the Ava I site chosen was:

| top strand: | CCCGAG |
| bottom strand: | GGGCTC |

This Ava I sequentially encoded a pro-glu dipeptide which is part of the desired polypeptide sequence. Upon assembly of this fragment into an array of repeated DNA fragments, the result was a perfect coding for the biopolymer with no amino acids other than those in the noted GG monomer sequence.

The two oligonucleotides, upon hybridization, formed a double stranded nucleic acid having cohesive ("sticky") ends for the restriction sites Eco RI and Sal I. Hybridization was carried out in a solution of tris(hydroxymethyl) aminomethane buffer (10 mmolar, pH 8), containing ethylenediaminetetraacetic acid (1 mmolar) and the oligonucleotides (20 µg/ml of each). Hybridization was begun at 95° C., and the reaction mixture was gradually cooled to 25° C. at a rate of 1° C./15 minutes. Hybridization was determined to be successful by analysis for the presence of a single narrow band of the correct double strand molecular weight upon electrophoresis in a conventional 6% polyacrylamide gel [using tris(hydroxymethyl)aminomethane, borate and ethylenediaminetetraacetic acid], or by a cooperative thermal denaturation observed by a hyperchromic increase in absorbance at 260 nm.

This hybridized fragment was then ligated into the Eco RI and Sal I sites of a modified derivative of the commercially available pTZ18R Genescribe plasmid that has a shortened polylinker consisting of Eco RI, Ava I, Sal I, Hind III (pSCW627), as shown in FIG. 1. This and other modified pTZ18R Genescribe derivatives are biopolymer cloning vectors, because this is where monomer DNA or repeated multimers are cloned after oligonucleotide hybridization (cloning of what is identified as "GG monomer DNA") or directional assembly (cloning of "multimer GG" DNA). Three such cloning vectors are pSCW627, pSCW1143, pSCW1253, as shown in FIG. 1. The plasmid pSCW627 was used for cloning the Eco RI-Sal I hybridized oligonucleotide pair, whereas pSCW1143 was used for the cloning of repeated GG monomer DNA to produce DNA encoding for the amino acid sequence Glu Phe Gly Lys Gly Pro Glu {[(Gly Pro Gln)(Gly Pro Glu)$_4$]$_2$}$_n$ wherein the underlined Lys is the lysine that ultimately will be cleaved in the biopolymer by Trypsin to remove the N-terminal FLAG™ epitope [the Asp Tyr Lys (Asp)$_4$ Lys FLAG™ epitope sequence is encoded by the yeast expression plasmid]. The N-terminal FLAG™ epitope generally provides for analytical detection by conventional anti-FLAG® monoclonal antibodies, M$_1$ or M$_2$, to the [Asp Tyr Lys (Asp)$_4$ Lys] FLAG™ epitope sequence in conjunction with the use of conventional Western blots.

Plasmid pSCW1253 was used for the "landing"(or cloning) of repeated GG monomer DNA that ultimately was used to secrete the biopolymer sequence Gly Pro Glu {[(Gly Pro Gln)(Gly Pro Glu)$_4$]$_2$}$_n$ devoid of the presence of any nonpolymer amino acids as used in pSCW1143 constructions (that is, the N-terminal FLAG™ epitope from the yeast expression plasmid, the amino acids encoded by the restriction enzyme site, Eco RI, and the Gly-Lys dipeptide for Trypsin cleavage).

The assembly of repetitive DNA monomers was separated into repeating multimers, and the potential recombination toxicity of direct repeats of DNA was separated from the actual production of the secreted amino acid biopolymer and the potential protein toxicity to the cell by using two different organisms (a prokaryote and an eukaryote). First, the repetitive DNA was initially cloned in E. coli with the reading frame of the inserts out of the reading frame of lacZ in the vectors pSCW627, pSCW1143 and pSCW1253. Second, the biopolymer was produced by secretion in the baker's yeast, S. cerevisiae.

A mixture of the hybridized GG monomer DNA as described above was ligated into the Eco RI and Sal I sites of pSCW627 with T4 DNA ligase at 16° C. for 16 hours by standard methods. The ligation reaction was then transformed into E. coli strain JM109 [genotype e14-(mcrA), recA1, endA1, gyrA96, thi-1, hsdR17(r$_k$-, m$_{k+}$), supE44, relA1, Δ(lac-proAB), (F' traD36, proAB, lacI$^q$ZΔM15)] that had been made competent by a standard calcium chloride procedure and stored at −80° C. (see *Molecular Cloning: A Laboratory Manual*, noted above). The transformation reaction was plated onto X-GAL (80 µg/ml) LB plus ampicillin (150 µg/ml) plates and incubated at 37° C. Transformants were picked into liquid LB plus ampicillin media, grown overnight at 37° C., and plasmid DNA prepared by standard methods.

The presence of clones containing inserts was analyzed by Eco RI-Sal I double digests and by Ava I solo digests. Clones containing the hybridized oligonucleotide insert were white, because the oligonucleotide Eco RI-Sal I fragment has an in-frame stop codon included between the last Ava I site and the Sal I site, which ensures a convenient X-GAL blue/white color transformation assay for the presence of the hybridized GG monomer.

A monomer fragment called "AG monomer", in which the encoded glutamines had been replaced by encoded asparagines, was also cloned in parallel.

Figure 2B:
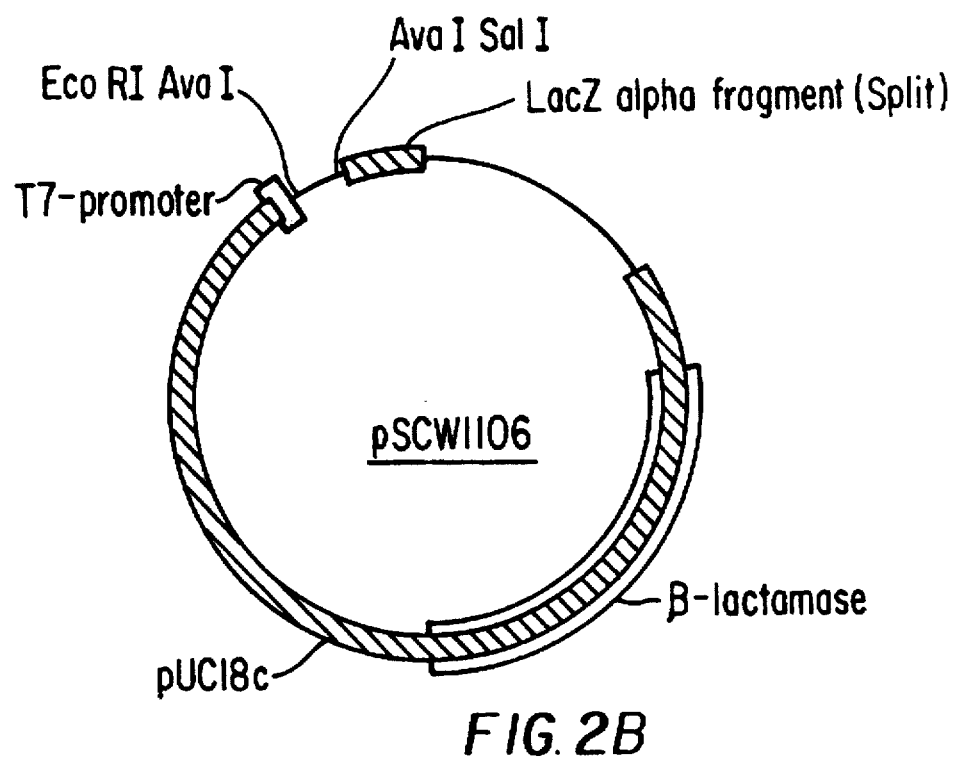

Two plasmids, pSCW1109 and pSCW1106 (see FIG. 2) were found to have putative monomer inserts of GG monomer and AG monomer, respectively, of the correct size, as determined using gel electrophoresis and conventional molecular weight markers. No evidence of plasmid instability due to recombination of the GG monomer or AG monomer inserts was observed.

The GG and AG monomers encoded in the two plasmids, pSCW1109 and pSCW1106, respectively, were found to match the desired encoded monomer sequence as determined by fluorescent DNA sequencing on a conventional Applied Biosystems 390 instrument using standard procedures.

The sequenced GG monomer DNA, inserted into pSCW627 and identified as pSCW1109 DNA is shown as follows in Schematic 1:

greater than 40 occurred, as determined by 0.7% w/v agarose electrophoresis. Size fractionated GG multimers were prepared: first, by separation on a preparative 0.7% agarose electrophoresis gel, secondly, by visualizing the bands by ethidium bromide staining and fluorescence, and thirdly, by cutting the multimer ladder distribution into agarose slices, each containing a given size pool of repeats of GG monomer, (3 to 6, 7 to 11, 12 to 17, 18 to 24, 25 to 33 and lastly to the top of the multimer distribution). Finally, each multimer DNA pool was purified from the agarose gel slice by the glass milk procedure (noted above).

Each size fractionated GG multimer pool was ligated by standard procedures at 16° C. overnight with T4 DNA ligase into pSCW1143 or pSCW1253 at the Ava I site (FIG. 1) which had been dephosphorylated by standard procedures with calf intestinal phosphatase or shrimp alkaline phosphatase. Dephosphorylation insures a greater percentage of Schematic 1 pSCW627

```
            >Eco R I    >Ava I
            |          |
            |          10        20        30        40        50        60
            |          *         *         *         *         *         *
Top strand:    GAATTCGGTCCCGAGGGTCCACAAGGTCCAGAAGGTCCAGAAGGTCCAGAAGGTCCAGAA
Bottom strand: CTTAAGCCAGGGCTCCCAGGTGTTCCAGGTCTTCCAGGTCTTCCAGGTCTTCCAGGTCTT >Ava I          >Sal I
                                              |               |
              70        80        90         100     Stop    110
              *         *         *           *       |       *
              GGTCCACAAGGTCCAGAAGGTCCAGAAGGTCCAGAAGGTCCCGAGCTAAGTCGAC
              CCAGGTGTTCCAGGTCTTCCAGGTCTTCCAGGTCTTCCAGGGCTCGATTCAGCTG
                                                              |
``` extra base to align this stop codon to the reading frame of the alpha
Lac Z start codon in the landing vector derived from pTZ18R Genescribe so
that there is a good blue to white screen for the presence of cloned inserts A sample (1 mg) of pSCW1109 DNA was prepared by the method of Lee et al from a culture grown in the noted medium including ampicillin (150 μg/ml). The Ava I monomer nucleic acid encoding the GG monomer was prepared by restricting the pSCW1109 DNA with 2 Units of Ava I per μg DNA at 37° C. for 8 hours. A complete digest was obtained as determined from the presence of two bands at 90 bp and 2.9 kbp on a conventional agarose gel. The Ava I monomer DNA was separated from the plasmid backbone by preparative 2% w/v agarose electrophoresis using a buffered solution containing tris(hydroxymethyl) aminomethane, phosphate and ethylenediaminetetraacetic acid, and visualized by ethidium bromide staining and fluorescence. The agarose strip containing the Ava I monomer DNA was cut out of the gel and purified by a glass milk procedure using US BIOCLEAN™ glass beads (available from US Biochemicals, Inc.) according to the instructions provided.

Multimers of the GG monomer (identified herein as "GG multimers") were prepared by self legating the GG monomer DNA with T4 DNA ligase under standard conditions at 16° C. until a distribution of polymer repeats from 2 to insert containing transformants when a single restriction site is used for cloning.

Figure 3:
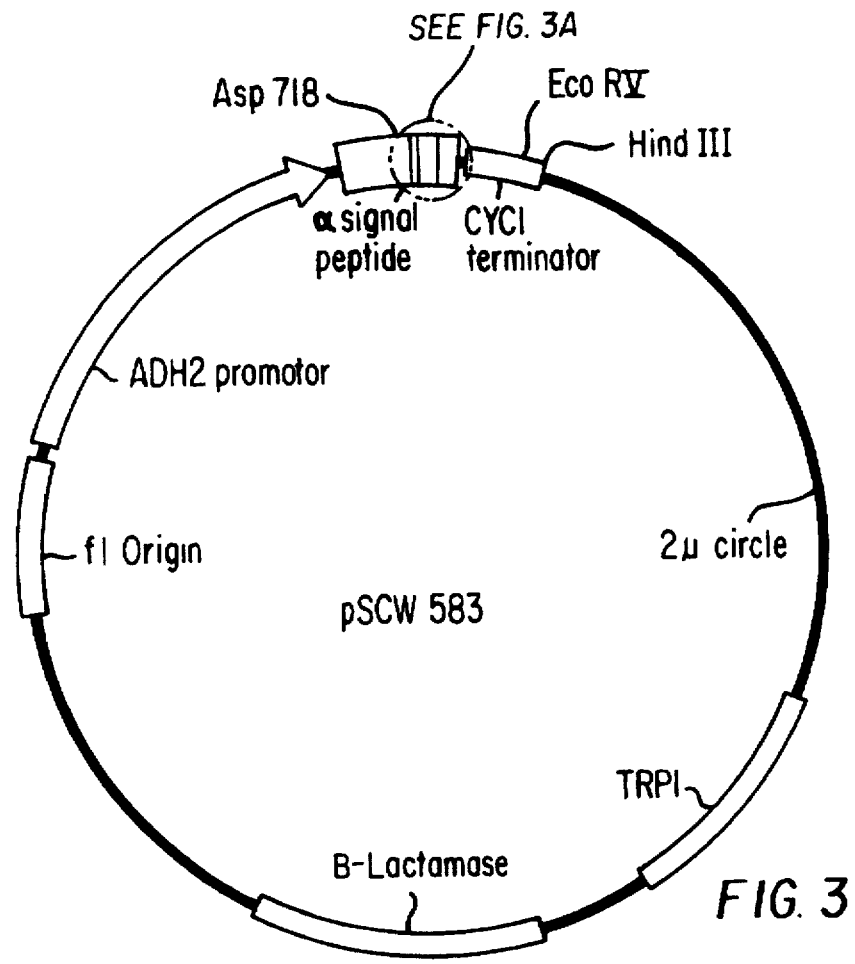
FIGS. 3 and 3A are a schematic diagram of the baker's yeast expression plasmid used in Example 1 below.
Figure 3A:
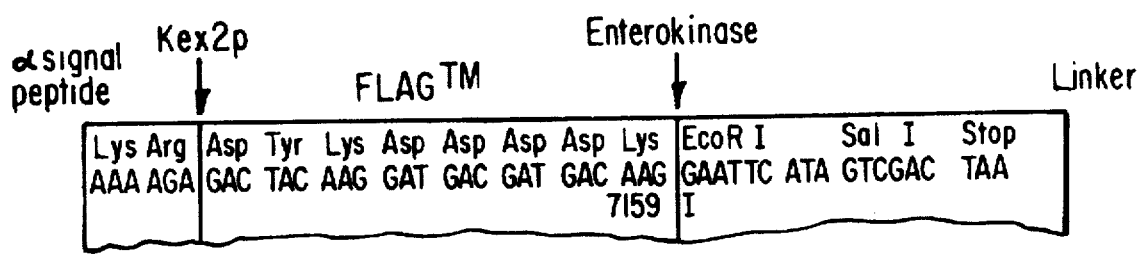

To produce the GG biopolymer having a FLAG™ epitope that is removable by Trypsin, the landing plasmid pSCW1143 is used. The plasmid encodes a lysine Trypsin cleavage site. Schematic 2 below (pSCW1143 linker) shows the reading frame that results from cloning of Eco RI-Sal I fragments containing Ava I multimers into the pSCW583 vector (FIG. 3), and not that in the lacZ reading frame of pSCW1143 (FIG. 1). This illustrates the distinction of biopolymer DNA construction in E. coli from biopolymer secreted expression in S. cerevisiae. This Ava I site CCC GAG sequence, at which repeated GG monomer is inserted, is preceded first by a glycine codon to produce a starting GPE tripeptide in the GG biopolymer and secondly by a lysine codon acid for cleavage by the Trypsin protease. The Ava I site that precedes the stop codon and thus the biopolymer, as constructed, ends in a Gly-Pro-Glu tripeptide.

Schematic 2 pSCW1143 extra glycine codon, GGT, so that the yeast produced biopolymer will start
with a glycine proline glutamic acid tripeptide since the Ava I encodes a
proline glutamic acid dipeptide

```
                                      Trypsin cleavage site
                                            |     |
              Glu  Phe  Gly  Lys  Gly  Pro  Glu  Stop
Top Strand:   GAA  TTC  GGT  AAG  GGT  CCC  GAG  TAA  GTC  GAC  AAG  CTT
Bottom strand:CTT  AAG  CCA  TTC  CCA  GGG  CTC  ATT  CAG  CTG  TTC  GAA
              |         *              |    *         |    *    |
              |         10             |    20        |    30   |
              >                        >              >         >
              Eco R I                  Ava I          Sal I     Hind III
                        10                  20             30
```

To produce the GG biopolymer without any extraneous amino acids, the landing plasmid pSCW1253 was used. The pSCW1253 plasmid encodes the C-terminus of the yeast alpha factor secretory leader peptide, from the Asp 718 site to the encoded Lys Arg Kex2p protease site. The Kex2p protease cleaves the alpha secretion factor on the C-terminus side of the Lys Arg pair. Schematic 3 below (pSCW1253) also shows the reading frame that results from cloning of Asp 718-Sal I fragment containing Ava I multimer fragments into pSCW583 (FIG. 3), and not that in the lacZ reading frame of pSCW1253 (FIG. 1). This again illustrates the distinction of biopolymer DNA construction in *E. coli* from biopolymer secreted expression in *S. cerevisiae*. The Ava I site, CCC GAC sequence, at which repeated GG monomer is inserted, follows first a glycine codon to produce a starting Gly-Pro-Glu tripeptide in the GG biopolymer and secondly a lys-arg codon pair as a Kex2p protease cleavage site. Additionally, a glutamic acid codon precedes the stop codons as part of the Ava I site, such that the biopolymer ends in a Gly-Pro-Glu tripeptide.

pSCW583 as Asp 718-Sal I DNA fragments. The result was GG multimer DNA that encodes and produces Gly Pro Glu{[(Gly Pro Gln)(Gly Pro Glu)$_4$]$_2$}$_n$ biopolymers upon secretion from yeast.

Each GG multimer pool ligation, whether landed in the Ava I of pSCW1143 or pSCW1253, was transformed into *E. coli* strain JM109 as previously described. The presence of clones containing inserts in pSCW1143 were analyzed for multimer size by Eco RI-Sal I double digests compared to molecular weight standards whereas clones containing inserts in pSCW1253 were analyzed for multimer size by Asp 718-Sal I double digests. Multimer insert containing clones were checked by Ava I solo digests for verification of correct multimer assembly and absence of recombination artifacts. Typically, greater than 80% of the colonies on the transformation plate contained clonal multimers. These clones were all observed to be uniformly stable with the complete absence of recombination artifacts. Additionally, all GG monomer or multimer clones (in pSCW1143 and pSCW1253 backbones) were a brilliant sapphire blue color Schematic 3 pSCW1253 extra glycine codon, GGT, so that the yeast produced biopolymer will start
with a glycine proline glutamic tripeptide since the Ava I encodes a proline
glutamic acid dipeptide

```
                         Kex2p protease cleavage site        tandem Stop codons
                                            |    |                   |
              ...  ...  ...  Val  Pro  Asp  Lys  Arg  Gly  Pro  Glu  Stop  Stop
GAA  TTC  CGG  GTA  CCA  GAT  AAG  AGA  GGT  CCC  GAG  TAA  TAA  GTC  GAC  AAG  CTT
CTT  AAG  GCC  CAT  GGT  CTA  TTC  TCT  CCA  GGG  CTC  ATT  ATT  CAG  CTG  TTC  GAA
|         |    *              *              |    *              *         |    *
|         |    10             20             |    30             40        |    50
|         |                                  |                             |
>         >                                  >                   >         >
Eco R I   Asp718                             Ava I               Sal I     Hind III
```

An Asp 718 site occurs in the yeast alpha factor signal secretion DNA sequence. The cleavage site for the yeast alpha signal protease, Kex2p (KEX2 gene product), is encoded in the yeast alpha factor signal DNA following this Asp 718 site. Therefore, a linker with an Asp 718 Sal I DNA fragment which encodes the amino acids normally found in the alpha factor secretion signal peptide from the Asp 718 up to the Kex2p cleavage site followed by the extra glycine codon and the appropriate Ava I site for landing GG multimers, was engineered. Biopolymer GG repeats were "landed" in this Ava I site, isolated and recloned into which was more intense than the blue of the non-insert containing plasmids (pSCW1143 and pSCW1253) in JM109 on LB X-Gal transformation plates.

Figure 4A:
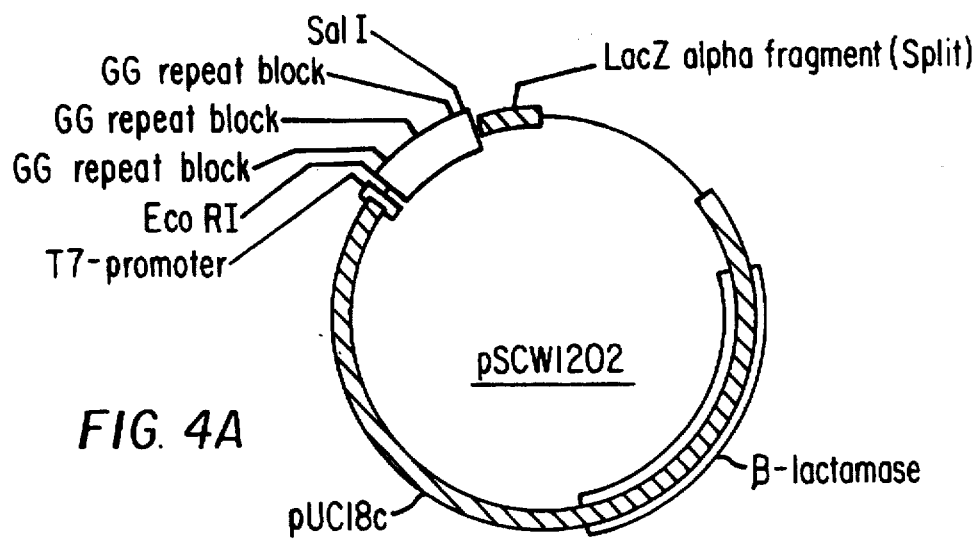
FIGS. 4A, 4B and 4C are a schematic diagram of the multimer plasmids used in the recombinant preparation of a collagen-type polypeptide, as described in Example 1 below.
Figure 4B:
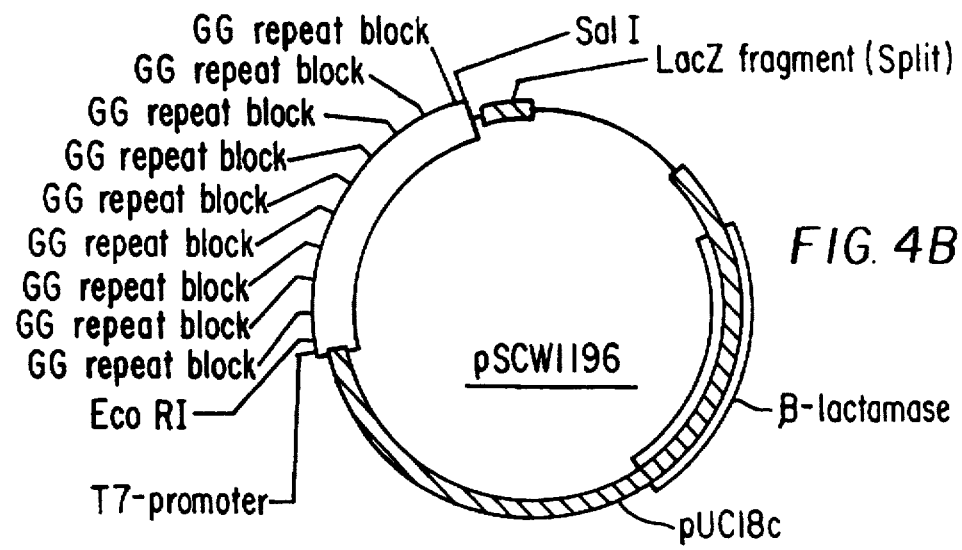
Figure 4C:
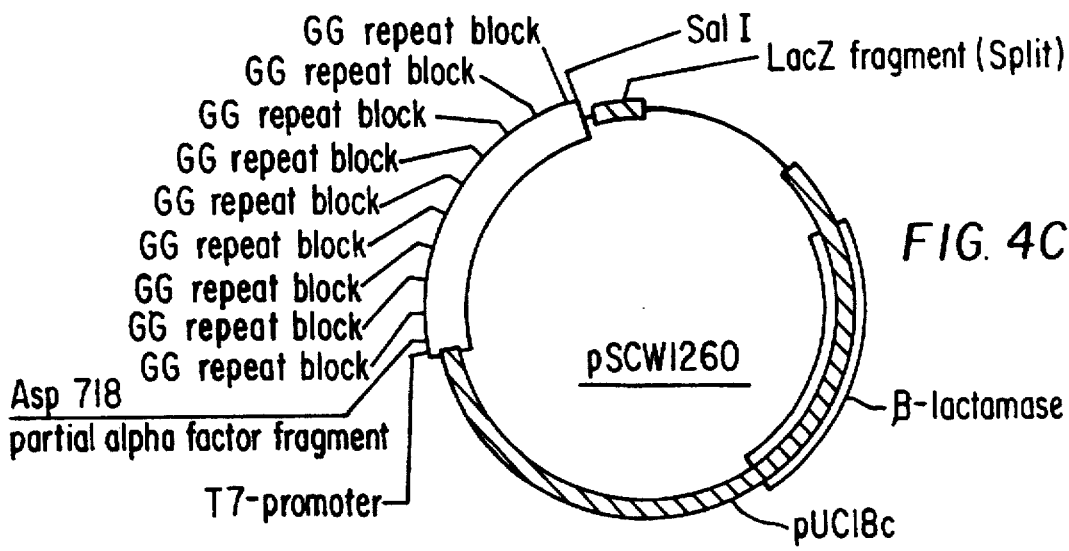

Two transformants in pSCW1143 backbones found to have the GG monomer DNA assembled into multimers of 3 and 9 were designated pSCW1202 and pSCW1196, respectively (FIG. 4). One transformant in a pSCW1253 backbone found to have the GG monomer DNA assembled into a multimer of 9 was designated pSCW1260 (FIG. 4).

The baker's yeast protein expression vector pSCW583 contained DNA encoding the yeast alcohol dehydrogenase II promoter for regulated high transcriptional mRNA expression, the alpha factor pre-pro-region for translational initiation and extracellular secretion, the Kex2p cleavage site to remove the alpha factor pre-pro-region from the biopolymer, the FLAG™ epitope, a short Eco RI-Sal I polylinker to clone the assembled biopolymer, a CYC1 bidirectional transcriptional mRNA terminator, the yeast TRP1 gene for selection in yeast, yeast 2 micron circle elements for high copy plasmid control in yeast, the *E. coli* bla gene for antibiotic selection in *E. coli*, and pBR322 elements for high copy control in *E. coli*.

Multimers pSCW1202 (3 repeats of the GG monomer) and pSCW1196 (9 repeats of the GG monomer) were used as the source of a Eco RI-Sal I DNA polymer block containing the repeated GG monomer DNA for ligation at the same sites into the *S. cerevisiae* protein expression vector, PSCW583. Ligation of these DNA fragments was by the previously described standard method. The ligation reactions were transformed into *E. coli* strain JM109 and the transformants selected for ampicillin resistance by the previously described standard methods.

pSCW1260 (9 repeats of the GG monomer) was used as the source of Asp 718-Sal I DNA polymer block containing the repeated GG monomer DNA for ligation at the same sites into the *S. cerevisiae* protein expression vector, pSCW583. Ligation of these DNA fragments was carried out by the previously described standard method. The ligation reactions were transformed into *E. coli* strain J M109 and the transformants selected for ampicillin resistance by the standard methods previously described.

Figure 5A:
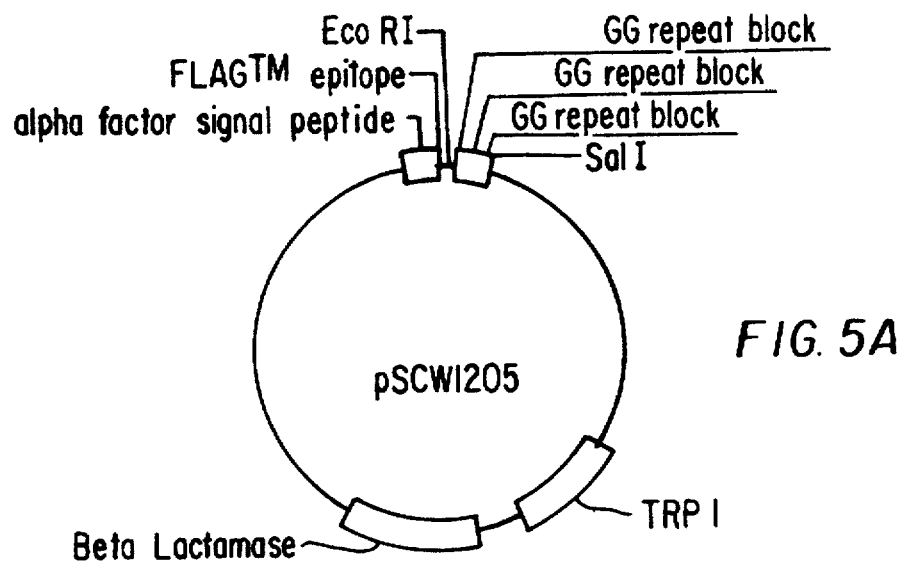
FIGS. 5A, 5B and 5C are a schematic diagram of the biopolymer yeast expression plasmids constructed and used in Example 1 below.
Figure 5B:
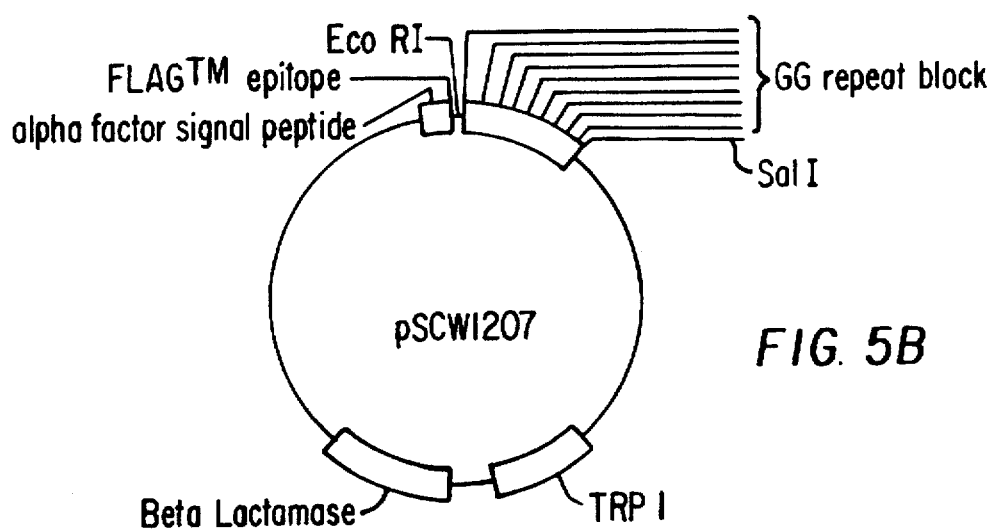
Figure 5C:
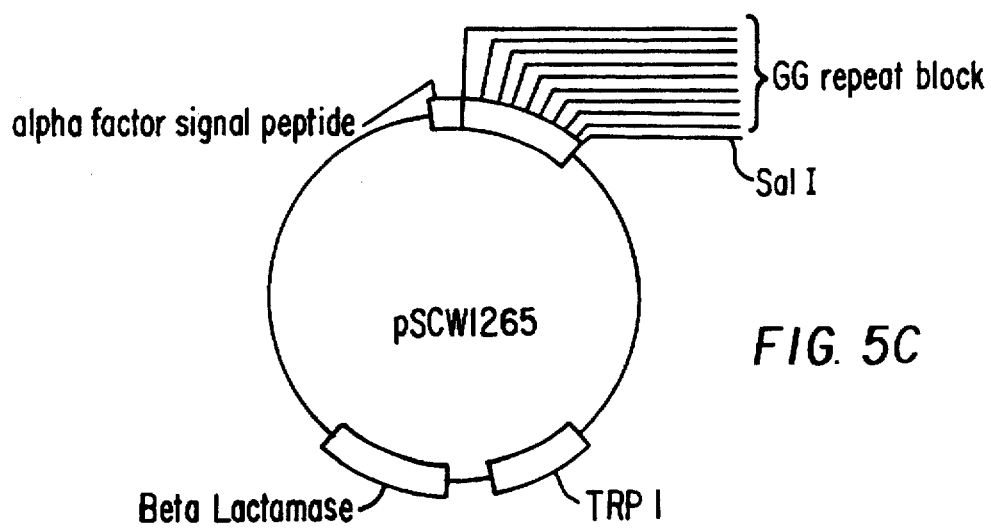

Transformants derived from the ligations of pSCW1202 and pSCW1196 multimer DNA (destined to be FLAG™ lysine epitope biopolymers) into the pSCW583 yeast expression vector were screened by Eco RI-Sal I double digests to confirm correct multimer size and by Ava I solo digests to confirm genetic stability. Two transformants were designated GG biopolymer yeast expression plasmids, pSCW1205 and pSCW1207 (FIG. 5). In yeast, pSCW1205 produces FLAG™ epitope Trypsin site N-terminally tagged 3 repeat GG biopolymer having the sequence:

---

SEQ ID NO:19:
Asp Tyr Lys (Asp)₄ Lys Glu Phe Gly Lys* Gly Pro Glu
{[(Gly Pro Gln) (Gly Pro Glu)₄]₂}₃,

--- while pSCW1207 produces the sequence:

---

SEQ ID NO:20:
Asp Tyr Lys (Asp)₄ Lys Glu Phe Gly Lys* Gly Pro Glu
{[(Gly Pro Gln) (Gly Pro Glu)₄]₂}₉.

---

In this example, after production and purification, the extra N-terminus amino acids of the biopolymer were removed by Trypsin digestion at the lysine*. The biopolymer was re-purified and processed to the form of SEQ ID NO:3.

Transformants derived from the ligation of pSCW1260 multimer DNA (destined to be SEQ ID NO:3), into the yeast expression vector pSCW583 were screened by Asp718-Sal I double digests to confirm correct multimer size and by Ava I solo digests to confirm genetic stability. One transformant was designated pSCW1205 (SEQ ID NO:19), pSDCW1207 (SEQ ID NO:20) and pSCW1265 (SEQ ID NO:3), were transformed by standard electroporation with a conventional Bethesda Research Electroporator into *S. cerevisiae* strain BJ3505 (available from the Yeast Genetic Stock Center, University of California, Berkeley). This strain has the genotype (mating type a pep 4::HIS3 prb1-1.6R HIS3 lys2-208 trp1-101 ura3-52 gal2 can1). The protease deficient properties of this strain are well known. The pep 4::HIS3 mutation inactivates the structural gene, PEP4, which encodes the PrA protease (an aspartic class endoprotease) whereas the prb1-1.6R mutation inactivates the structural gene, PRB1, which encodes the PrB protease (a serine class subtilisin-like endoprotease). Both PrA and PrB are lumenal vacuolar proteases. PrB in particular is expressed at high levels in stationary culture conditions.

Transformants were selected for TRP1 complementation on Synthetic Complete media (minus tryptophan) plates by standard methods (*Methods in Yeast Genetics Laboratory Manual*, Cold Spring Harbor Press, 1981 and *Guide to Yeast Genetics and Molecular Biology*, Methods in Enzymology, Vol. 194, Academic Press, Inc., 1991).

BJ3505 transformants of pSCW1205, pSCW1207 and pSCW1265 were first grown for 48 hours on a roller at 30° C. to early stationary phase in 5 ml of liquid Synthetic Complete (minus tryptophan) media. These cultures were then rediluted to 1% v/v in 50 ml of the same media and grown on a rotary shaker at 175 revolutions per minute to early stationary phase (about 8 OD units at 600 nm) at 30° C. Finally, the culture were diluted to 4% by volume into one liter of production media and grown for 70 hours on a rotary shaker at 175 revolutions per minute at 30° C. in a 2.8 liter baffled fernbach flask. Several different production media may be used with or without the addition of calcium as a counter ion for the biopolymer and/or the yeast cell wall. YP1 production media contained 10% w/v yeast extract, 20% w/v Bactopeptone, 1% w/v dextrose and 3% w/v glycerol. YP4 production media contained 10% w/v yeast extract, 80% w/v Bactopeptone, 1% w/v dextrose and 3% w/v glycerol. Either a YP1 or YP4 optimized media supplemented with calcium chloride (20 millimolar) can be used for high production of GG biopolymers. YP1 production media supplemented with 20 mmolar calcium chloride provided a preferable compromise of high expression (about 500 mg/l) and low background of media protein impurities.

A pseudo plasticity in the GG biopolymer production culture was observed in some cases at 24 hours of culture growth when carefully examined and compared to a negative control culture. This pseudo plasticity rheologically shear thins when the culture was stirred with a rod. The pseudo plasticity occurs in a time dependent culture growth state only upon high level secreted expression of the SEQ ID NOS:1, 2, 3, 19 and 20 biopolymers (with or without the FLAG™ N-terminus epitope) and not for other secreted proteins. This phenomenon was observed much more easily in partially or purified GG biopolymer fractions. It is biopolymer length, concentration, temperature and ionic strength dependent, and lowers the specific gravity of the production culture broth compared to a negative control culture.

The purification of SEQ ID NO:20 (pSCW1207 in *S. cerevisiae* strain BJ3505) and the removal of the FLAG™ epitope to produce SEQ ID NO:3 is described below. Twenty liters of broth from BJ3505 transformed with pSCW1207 was prepared from twenty separate one liter fernbach cultures grown by the YP1 culture conditions described above. To remove the yeast cells and produce a culture supernatant (S1), the 20 liters of culture broth were centrifuged at 10,000 g for 10 minutes. The supernatant was sometimes filter sterilized using a 1,000,000 molecular weight cutoff conventional Filtron tangential flow filtration unit to produce a second supernatant (S2), that was devoid of yeast cells.

Twenty liters of either S1 or S2 were brought to pH 3.2 with hydrochloric acid to precipitate (overnight at 4° C.) the biopolymer preferentially over the other broth components. The acidified supernatants of S1 or S2 were centrifuged at 10,000 g for 20 minutes to produce a supernatant (S3) that was discarded, and a pellet (P3) containing the desired biopolymer. The P3 pellet was then resuspended in 2 liters (one tenth the original culture volume) of tris (hydroxymethyl)amino methane buffer (50 molar, pH 7.8) containing sodium chloride (200 molar), ethylenediamine-tetraacetic acid (20 mmolar) and phenylmethylsulfonyl fluoride (1 mmolar) and clarified by centrifugation at 10,000 g for 20 minutes. The desired biopolymer (SEQ ID NO:20) was in the supernatant (S4), and the residual pellet (P4) was discarded.

The biopolymer was purified by ion exchange chromatography. The S4 supernatant was applied to a commercial 10 cm×30 cm (4 liter) DEAE Sephacel ion exchange column. The column was washed with 80 liters (20 column volumes) of tris(hydroxymethyl)aminomethane buffer (50 molar, pH 7.8) containing sodium chloride (200 mmolar) at a flow rate of 3 liters per hour and a pressure of 0.3 atmospheres until the eluant had an absorbance less than 0.001 OD at 214 nm. The FLAG™ GG 9-mer (SEQ ID NO:20) was eluted at a flow rate of 3 liters/hour with a step gradient of buffer (50 mmolar, pH 7.8) containing sodium chloride (375 mmolar) in 500 ml fractions into 4 liters. The fractions containing the biopolymer, as determined by conventional SDS acrylamide electrophoresis, were pooled and designated fraction F1.

The FLAG™ N-terminal epitope was removed by Trypsin proteolytic cleavage at the C-terminal side of the lysine* immediately proceeding the first repeating tripeptide (GPE) in the biopolymer to produce a cleaved unwanted peptide and the desired SEQ ID NO:3. To cleave the epitope, a sample (1 g) of fraction F1 was reacted with 400 units Trypsin (type XI DPCC treated) per mg of biopolymer per ml of calcium chloride (20 mmolar) in buffer (100 mmolar, pH 8.5) at 37° C. for 18 hours. The reaction was completely dependent upon the presence of calcium chloride. The completeness of the reaction was determined to be essentially 100% by estimating the relative mobility on SDS gels of the Trypsin treated sample relative to the mobility of the starting fraction F1. The Trypsin cleaved biopolymer migrated faster on SDS acrylamide electrophoresis than the uncleaved biopolymer with a relative Rf of 1.10. The Trypsin cleaved biopolymer reaction solution was designated fraction F2. The use of Trypsin additionally provides a means to remove potential trace amounts of protein that are not detectable by standard analytical means such as absorbance at 280 nm, Coomassie Blue R-250 staining of SDS electrophoresis gels, GHOST Bands™ Protein Detection System (Promega Corporation) or silver staining of SDS electrophoresis gels.

The apparent molecular weights determined from the SDS gel migration distances relative to the molecular weight markers for the uncleaved and the cleaved biopolymers were 40 kd and 38 kd, respectively. The calculated molecular weights from the primary amino acid sequence are 27,177 daltons and 25,778 daltons, respectively. It is known for collagen and gelatin fragments that their apparent molecular weight is about 1.4 times larger than their true primary sequence molecular weight ("Estimation of the Size of Collagenous Proteins by Electrophoresis and Gel Chromatography", *Methods in Enzymology*, 1982, Vol. 82, Section 19, pp. 410–423). The ratio of the apparent molecular weight to the primary sequence molecular weight for the uncleaved and cleaved biopolymers was about 1.47 and is thus consistent with the known anomalous molecular weight behavior of collagen and gelatin fragments.

SEQ ID NO:3 stained pink with Coomassie Blue R-250 in a transitory manner only during the early phase of destaining in 10% acetic acid and 5% methanol, and at the end point of destaining, was not visible at all. The FLAG™ epitope on the biopolymer (SEQ ID NO:20) serves to enable detection by Coomassie Blue R-250 staining. However, the FLAG™ epitope did not enable detection by M1 or M2 monoclonal antibodies on Western blots of SDS gels. Therefore to detect the processed biopolymer without the FLAG™ epitope, SDS gels were visualized using a commercially available negative stain utilizing copper containing solutions (GHOST BANDS™ Protein Detection System).

Alternatively, to reproducibly and conveniently detect the FLAG™-containing biopolymer, the cationic carbocyanine dye, 4,5,4',5'-dibenzo-3,3'-diethyl-9-methyl-thiacarbocyanine bromide (also known as "Stains-All") was used. The noted biopolymer stained a chrome blue-green color against a pink background.

SEQ ID NO:3 from fraction F2 was purified on a FRACTOGEL™ tentacle polymer ion exchange matrix (from EM Separations, Division of EM Industries, Inc.). One gram of Trypsin cleaved biopolymer in 1 liter of fraction F2 reaction buffer mix was brought to a final ethylenediaminetetraacetic acid concentration (40 mmolar) and applied to a 5×30 cm (0.5 liter) DMAE FRACTOGEL™ tentacle polymer ion exchange column in tris(hydroxymethyl)aminomethane (50 mmolar, pH 8.0) containing sodium chloride (50 mmolar) at a cross sectional flow rate of 45 ml/hour/cm². The addition of ethylenediaminetetraacetic acid (40 mmolar) complexed the calcium chloride (20 mmolar) from the fraction F2 reaction buffer mix. The calcium chloride was observed to cause elution of the SEQ ID NO:3 biopolymer at variable sodium chloride concentrations from the FRACTOGEL™ tentacle polymer ion exchange matrix. The cleaved FLAG™ peptide and Trypsin self-digestion peptide fragments were eluted with 4 column volumes of tris(hydroxymethyl) aminomethane buffer (50 mmolar, pH 8.0) containing sodium chloride (300 mmolar), as assayed by a very low ratio of $A_{214}/A_{280}$ of less than 5.

Residual uncleaved biopolymer was eluted with 2 column volumes in half column volume steps of buffer (50 mmolar, pH 8.0) containing sodium chloride (400 mmolar) as assayed by a low ratio of $A_{214}/A_{280}$ of 41. SEQ ID NO:3 was eluted in a pure form with 2 column volumes in half column volume, steps of buffer (50 mmolar, pH 8.0) containing sodium chloride (600 mmolar) as assayed by a very high ratio of $A_{214}/A_{280}$ Of 281. The fractions containing the pure biopolymer were pooled and designated fraction F3.

In order to prepare and purify the biopolymer in a form suitable for use in photographic silver halide emulsions, including the controlled formation of silver halide crystals containing tabular or other morphologies, the biopolymer was dialyzed until the residual ions were potassium cations and nitrate anions. At the concentrations involved, these ions do not change the photographic properties of silver halides, whereas the original buffer, a primary amine, may affect them. A sample (750 mg) of pure SEQ ID NO:3 biopolymer fraction F3 (at a concentration of 1 mg/ml) was brought to a final concentration of ethylenediaminetetraacetic acid (20 mmolar) and dialyzed in SPECTRAPOR Seven 3,500 molecular weight, low metal and low sulfur containing dialysis tubing three times with 20 liters of deionized water (18 Megaohms/cm), 2 times with 1 mmolar potassium nitrate and two times with deionized water (18 Megaohms/ cm). The dialyzed pure biopolymer was freeze dried into a fluffy white powder and designated as fraction F4.

To prepare the dialyzed pure biopolymer in a form suitable for silver halide application, it was desalted by gel chromatography to remove excess potassium and nitrate counter ions. The dialyzed fraction F4 (750 mg) was dissolved (about 0.75 % w/v) into 98 ml of 0.22 μm filtered deionized water, warmed to 45° C. and held at that temperature for 30 minutes. It was then applied at a cross sectional flow rate of 45 ml/hour/cm$^2$ onto a 5 cm×18 cm (0.5 liter) G-25 Sephadex column in 0.22 μm filtered deionized water. The column was eluted in 0.22 μm filtered deionized water (18 Megaohms/cm) in a drop-wise manner into 8 ml constant drop fractions. The use of 0.22 μm filtered deionized water (18 Megaohms/cm) eliminates the possibility of particulate contaminants that might affect nucleation, growth, or photographic sensitivity, of silver halide grains, including tabular grains. The G-25 desalted biopolymer eluted as expected for classical desalting chromatography at the excluded volume and with some tailing past the void volume. Strikingly, the constant drop fractions containing the G-25 desalted pure biopolymer had almost a 15% increase in volume (about 9.2 ml) compared to fractions containing water or residual desalted ions (8 ml). Constant drop fractions were pooled beginning at the excluded volume which contained pure SEQ ID NO:3 (as determined by a high ratio of $A_{214}/A_{280}$ of 281) until the fractions began to show an increase in conductivity due to the emergence of ion impurities at the void volume (as determined by conductivity). The yield was determined by the use of a molar absorption constant at 214 nm of 241,000, based on the molar absorption constant at 214 nm of the GG monomer, 26,777, scaled to the molecular weight of the GG biopolymer. Later, this molar absorption constant was determined directly on the biopolymer and found to be accurate. A total of 675 m g of desalted pure biopolymer was recovered. The liquid desalted pure biopolymer was designated fraction F5.

To deliver the liquid desalted pure biopolymer in a convenient form for photographic emulsion precipitation, fraction F5 was freeze dried. Upon freeze drying, it became a clear transparent film that did not shatter but could be torn with the release of fibrils along the torn edges. The freeze dried desalted pure biopolymer was designated fraction F6.

The freeze dried desalted pure biopolymer was characterized at the Analytical and Synthetic Facility, Cornell Biotechnology Center, for amino acid composition by standard means of acid hydrolysis, ion chromatography and fluorescent detection. The following analysis was determined:

| Amino Acid | pMolar |
|---|---|
| Asx | 88.3 |
| Glx | 4830 |
| Ser | 11.4 |
| Gly | 4820 |
| His | <5 |
| Arg | 6.8 |
| Thr | 14.2 |
| Ala | 16.2 |
| Pro | 4850 |
| Tyr | 18.8 |
| Val | 6.8 |
| Met | 9.7 |
| Cys | <10 |
| Ile | <5 |
| Leu | 6.5 |

-continued

| Amino Acid | pMolar |
|---|---|
| Phe | 25.2 |
| Lys | 51.7 |

SEQ ID NO:3 was found to have an amino acid composition of glycine, proline and glutamic acid in a 1:1 molar ratio. This composition is consistent with the predicted amino acid composition since glutamines deamidate during the acid hydrolysis sample preparation. To crudely estimate the purity of the biopolymer in this sample, one can add the amounts of all amino acids present that are not contained by the biopolymer and divide by the amount of amino acids contained by the biopolymer. The result is a purity of at least 98.6%.

The freeze dried desalted pure biopolymer was also characterized by the Analytical and Synthetic Facility, Cornell Biotechnology Center for the N-terminus amino acid sequence. It was found to have an amino acid sequence as predicted beginning after the lysine for Trypsin cleavage through the next 40 amino acids. The three glutamines in the first 40 amino acids were found to be fully amidated. It is likely that the remaining encoded glutamines in the biopolymer are amidated glutamines as well.

The FLAG™ containing biopolymer (SEQ ID NO:20) was also characterized by N-terminus amino acid sequencing. It was found to have an amino acid sequence beginning with the FLAG™ epitope and then through the first 40 amino acids of the biopolymer. This demonstrates that upon secretion of this biopolymer the Kex2p protease correctly cleaved at the C-terminal side of the encoded Lys-Arg cleavage site to correctly expose a free N-terminal FLAG™ epitope. The inability to detect the biopolymer by the M1 or M2 FLAG™ anti-antibody on Western blots as previously described is therefore for some other reason than the mere absence of the target epitope.

The freeze dried desalted pure biopolymer was also characterized at the Analytical and Synthetic Facility for molecular weight by laser desorption mass spectrometry on a commercially available FinniganMat instrument. It was found to have a molecular weight of 26,001 daltons. This agrees well (within experimental error) with the predicted 25,778 daltons. The difference in molecular weights may be because of 4 or 5 residual strongly bound calcium ions.

EXAMPLE 2

Best Mode of the Invention

The biopolymer SEQ ID NO:3 was prepared using yeast host cells as described in Example 1. This example describes a preferred purification method of this invention.

The purification of SEQ ID NO:3 (pSCW1265 in *S. cerevisiae* strain BJ3505) is described below. Twenty liters of broth from BJ3505 transformed with pSCW1265 was prepared from twenty separate one liter fernbach cultures grown by the YP1 culture conditions described above. To remove the yeast cells and produce a culture supernatant (S1), the 20 liters of culture broth were centrifuged at 10,000 g for 10 minutes.

Twenty liters of S1 were brought to pH 3.2 with hydrochloric acid to precipitate (overnight at 4° C.) SEQ ID NO:3 preferentially over the other broth components. The acidified supernatant of S1 was centrifuged at 10,000 g for 20 minutes to produce a supernatant (S2) that was discarded, and a pellet (P2) containing the desired biopolymer. The P2 pellet was then resuspended in 2 liters (one tenth the original culture volume) of tris(hydroxymethyl)amino methane buffer (100 molar, pH 7.8) containing calcium chloride (20 molar). This suspension of P2 was then heated to 60° C. for at least 15 minutes, cooled to 37° C., and trypsin (400 units/mg of biopolymer, type XI, DPCC treated) was added and reacted for 48 hours at 37° C. Ethylenediaminetetraacetic acid (40 molar, pH 8.0) was added to the P2 resuspension, and the resulting solution was clarified by centrifugation at 10,000 g for 20 minutes. The desired biopolymer (SEQ ID NO:3) was in the supernatant (S3), and the residual pellet (P3) was discarded.

The SEQ ID NO:3 biopolymer was purified by ion exchange chromatography. The S3 supernatant was applied to a commercial 10 cm×30 cm (4 liter) DEAE Sephacel ion exchange column. The column was washed with 80 liters (20 column volumes) of tris(hydroxymethyl)aminomethane buffer (50 molar, pH 7.8) containing sodium chloride (300 molar) at a flow rate of 3 liters per hour and a pressure of 0.3 atmospheres until the eluant had an absorbance less than 0.001 OD at 214 nm. The SEQ ID NO:3 biopolymer was eluted at a flow rate of 3 liters/hour with a step gradient of buffer (50 molar, pH 7.8) containing sodium chloride (425 mmolar) in 500 ml fractions into 4 liters. The fractions containing the biopolymer, as determined by conventional SDS acrylamide electrophoresis (visualized as follows), were pooled, heated at 60° C. for 15 minutes, cooled, and designated fraction F1.

The biopolymer was visualized by staining with the cationic carbocyanine dye 4,5,4',5'-dibenzo-3,3'-diethyl-9-methyl-thiacarbocyanine bromide (also known as "Stains-All") was used. The noted biopolymer stained a chrome blue-green color against a pink background.

The apparent molecular weight of SEQ ID NO:3, as determined from the SDS gel migration distance relative to the molecular weight markers, was 38 kd. The calculated molecular weight from the primary amino acid sequence is 25,778 daltons. It is known for collagen and gelatin fragments that their apparent molecular weight is about 1.4 times larger than their true primary sequence molecular weight ("Estimation of the Size of Collagenous Proteins by Electrophoresis and Gel Chromatography", Methods in Enzymology, 1982, Vol. 82, Section 19, pp. 410–423). The ratio of the apparent molecular weight to the primary sequence molecular weight for the SEQ ID NO:3 biopolymer was about 1.47 and is thus consistent with the known anomalous molecular weight behavior of collagen and gelatin fragments.

SEQ ID NO:3 from fraction F1 was purified by hydrophobic exchange chromatography. The fraction F1 was brought to 20% w/v ammonium sulfate and applied to a commercial 2.5×10 cm Phenyl Sepharose column equilibrated in 20% w/v ammonium sulfate. The phenyl sepharose column containing the bound biopolymer was washed with 20 column volumes of 20% w/v ammonium sulfate. The column was eluted with descending 2% w/v ammonium sulfate steps in 2 column volume steps and then lastly with 2 column volumes of water.

The eluted biopolymer was detected as described above by conventional SDS acrylamide electrophoresis, and staining with the cationic carbocyanine dye. The eluted fractions containing the biopolymer, that is the low % w/v ammonium sulfate fraction of 2%, and the water elution fraction, were pooled and designated fraction F2.

In order to prepare and purify the biopolymer in a form suitable for use in photographic silver halide emulsions, including the controlled formation of silver halide crystals containing tabular or other morphologies, the biopolymer was dialyzed until the residual ions were potassium cations and nitrate anions. At the concentrations involved, these ions do not change the photographic properties of silver halides, whereas the original buffer, a primary amine, may affect them. A sample (750 m g) of pure SEQ ID NO:3 biopolymer fraction F2 (at a concentration of 1 m g/ml) was brought to a final concentration of ethylenediaaminetetraacetic acid (20 mmolar) and dialyzed by tangential flow diafiltration on a commercially available (Filtron) device equipped with a 30 kd cutoff filter one time with 20 liters of a potassium chloride solution (10 mmolar), 2 times with 1 mmolar potassium nitrate and two times with deionized water (18 Megaohms/cm). The dialyzed pure biopolymer was vacuum dried into a fluffy white powder and designated as fraction F4.

The freeze dried desalted pure biopolymer (fraction F4) was characterized at the Analytical and Synthetic Facility, Cornell Biotechnology Center, for amino acid composition by standard means of acid hydrolysis, ion chromatography and fluorescent detection. The following analysis was determined:

| Amino Acid | pMolar |
| --- | --- |
| Asx | 12.5 |
| Glx | 5577 |
| Ser | 18.4 |
| Gly | 5514 |
| His | <5 |
| Arg | <5 |
| Thr | 9.8 |
| Ala | <5 |
| Pro | 5658 |
| Tyr | <5 |
| Val | <5 |
| Met | 6.7 |
| Cys | <10 |
| Ile | <5 |
| Leu | <5 |
| Phe | <5 |
| Lys | <5 |

SEQ ID NO:3 was found to have an amino acid composition of glycine, proline and glutamic acid in a 1:1:1 molar ratio. This composition is consistent with the predicted amino acid composition since glutamines deamidate during the acid hydrolysis sample preparation. To crudely estimate the purity of the biopolymer in this sample, one can add the amounts of all amino acids present that are not contained by the biopolymer, less the values of a water blank control, and divide by the amount of amino acids contained by the biopolymer. The result is a purity of at least 99.76%. This is about 70 times more pure than obtained in Example 1.

The biopolymer was also characterized by the Analytical and Synthetic Facility, Cornell Biotechnology Center for the N-terminus amino acid sequence. It was found to have an amino acid sequence as predicted beginning at the glycine-proline-glutaric acid tripeptide through the next 40 amino acids. The three glutamines in the first 40 amino acids were found to be fully amidated. It is likely that the remaining encoded glutamines in the biopolymer are amidated glutamines as well.

The invention has been described in detail with particular reference to preferred embodiments thereof, but it will be understood that variations and modifications can be effected within the spirit and scope of the invention.

We claim:

1. A method for preparing and isolating a recombinant water-soluble collagen polypeptide comprising the steps of:
   A) preparing and expressing a water-soluble collagen polypeptide in a yeast host cell culture containing yeast host cells using recombinant DNA technology, said culture comprising from about 10 to about 30 mmol of calcium ions,
   B) after centrifugation or diafiltration of said culture to remove said yeast host cells, isolating said expressed water-soluble collagen polypeptide from the supernatant by isoelectric precipitation at a pH which is within ±1 pH unit of the isoelectric point of said water-soluble collagen polypeptide,
   C) after centrifugation of the supernatant obtained in step B, resuspending the resulting pellet in a buffer,
   D) after centrifugation of the buffered solution formed in step C, subjecting the supernatant thereby obtained to ion exchange chromatography to capture said water-soluble collagen polypeptide,
   E) obtaining at least one elution fraction and subjecting it to either hydrophobic interaction chromatography or a second ion exchange chromatography, and
   F) recovering said water-soluble collagen polypeptide from at least one elution fraction obtained in step E,
   wherein between steps B and E, treating said water-soluble collagen polypeptide, independently, with a calcium salt and a protease.

2. The method of claim 1 further comprising step G wherein said elution fraction obtained in step E is subjected to diafiltration for replacing ions in said elution fraction with different ions.

3. The method of claim 1 wherein, anytime between steps A and F, said water-soluble collagen polypeptide is heated to at least 45° C. for at least 10 minutes.

4. The method of claim 1 wherein said yeast host cell is a Saccharomyces genus.

5. The method of claim 4 wherein said yeast host cell is *Saccharomyces cerevisiae*.

6. The method of claim 1 wherein the pH during isoelectric precipitation is controlled without the addition of pH control agents.

7. The method of claim 1 wherein calcium ion is complexed with a calcium ion chelating agent during or after step C.

8. The method of claim 7 wherein calcium ions are complexed during step C.

9. The method of claim 1 wherein treatment with said protease and calcium salt occurs in step C.

10. The method of claim 1 wherein at least two salt washes are carried out in step D during said ion exchange chromatography.

11. The method of claim 1 wherein a salt solution comprising ammonium sulfate is used in step E.

12. The method of claim 1 wherein said recovered water-soluble collagen polypeptide is freeze dried.

13. The method of claim 12 wherein prior to freeze drying, the ions in the elution fraction obtained in step F are replaced with different ions.

14. The method of claim 1 wherein said yeast host cell culture comprises from about 20 to about 30 mmol of calcium ions.

15. A method for preparing and isolating a recombinant water-soluble collagen polypeptide comprising the steps of:
   A) preparing and expressing a water-soluble collagen polypeptide in a culture of *Saccharomyces cerevisiae* cells using recombinant DNA technology, said culture comprising from about 10 to about 30 mmol of calcium ions,
   B) after centrifugation of said culture to remove said cells, isolating said expressed water-soluble collagen polypeptide from the supernatant by subjecting the resulting supernatant to isoelectric precipitation at a pH of from about 3 to about 4,
   C) after centrifugation of the supernatant obtained in step B, resuspending the resulting pellet in a buffered solution of a calcium salt,
   C1) after heating said buffered solution to at least about 45° C. for at least 10 minutes, mixing said solution with a protease to form a proteolytic solution having a pH of from about 7 to about 9,
   D) after centrifugation of said solution, subjecting the supernatant thereby obtained to step gradient ion exchange chromatography to capture said water-soluble collagen polypeptide using buffered solutions of sodium chloride and a DEAE chromatography column,
   E) after heating at least one elution fraction obtained in step D to at least about 45° C. for at least 10 minutes, and subsequently cooling, subjecting said heated and cooled elution fraction to hydrophobic interaction chromatography using ammonium sulfate solutions and a phenyl sepharose chromatography column,
   E1) subjecting at least one elution fraction obtained in step E to diafiltration to replace ions in said elution fraction with different ions, and
   F) recovering said water-soluble collagen polypeptide from the resulting diafiltered elution obtained in step E1, and
   F1) vacuum drying said recovered water-soluble collagen polypeptide.

16. The method of claim 15 wherein said diafiltration in step E1 is carried out against salts compatible with photographic silver halide emulsions.

17. The method of claim 15 wherein said protease is trypsin.

18. A method for preparing and isolating a recombinant water-soluble collagen polypeptide comprising the steps of:
   A) preparing and expressing a water-soluble collagen polypeptide in a culture of *Saccharomyces cerevisiae* cells using recombinant DNA technology, said culture comprising from about 10 to about 30 mmol of calcium ions,
   B) after centrifugation or diafiltration of said culture to remove said cells, isolating said expressed water-soluble collagen polypeptide from the supernatant by subjecting the resulting supernatant to isoelectric precipitation at a pH of from about 3 to about 4,
   C) after centrifugation of the supernatant obtained in step B, resuspending the resulting pellet in a buffered salt solution, said solution having a pH of from about 7 to about 9,
   D) after centrifugation of said buffered salt solution, subjecting the supernatant thereby obtained to a first step gradient ion exchange chromatography to capture said water-soluble collagen polypeptide using buffered solutions of sodium chloride and a DEAE chromatography column,
   D1) adding a buffered solution of a calcium salt and a protease to at least one elution fraction obtained in step D to form a proteolytic solution,
   D2) adding a calcium ion chelating agent to said proteolytic solution,
   E) subjecting said proteolytic solution to a second step gradient ion exchange chromatography using sodium chloride solutions and a DMAE chromatography column,
   E1) subjecting at least one elution fraction obtained in step E to diafiltration to replace ions in said elution fraction with different ions,
   F) recovering said water-soluble collagen polypeptide from the resulting diafiltered elution fraction obtained in step E1, and
   F1) vacuum drying said recovered water-soluble collagen polypeptide.

19. The method of claim 18 wherein said protease is trypsin.

20. The method of claim 18 wherein said diafiltration in step E1 is carried out against salts compatible with photographic silver halide emulsions.

21. A method for preparing and isolating a recombinant water-soluble collagen polypeptide comprising the steps of:
   A) preparing and expressing a water-soluble collagen polypeptide in a yeast host cell culture containing yeast host cells using recombinant DNA technology, said culture comprising from about 10 to about 30 mmol of calcium ions,
   B) after centrifugation or diafiltration of said culture to remove said yeast host cells, isolating said expressed water-soluble collagen polypeptide from the supernatant by isoelectric precipitation at a pH which is within ±1 pH unit of the isoelectric point of said water-soluble collagen polypeptide,
   C) after centrifugation of the supernatant obtained in step B, resuspending the resulting pellet in a buffer,
   D) after centrifugation of the buffered solution formed in step C, subjecting the supernatant thereby obtained to ion exchange chromatography to capture said water-soluble collagen polypeptide, E) obtaining at least one elution fraction and subjecting it to either hydrophobic interaction chromatography or a second ion exchange chromatography, and F) recovering said water-soluble collagen polypeptide from at least one elution fraction obtained in step E, wherein between steps B and E, treating said water-soluble collagen polypeptide, independently, with a calcium salt and a protease, wherein said water-soluble collagen polypeptide comprises two or more occurrences of the Gly-Pro-Y triplet, wherein Y is Gln, Glu, Met, Ile, His, Lys, Asn or Tyr.

22. A method for preparing and isolating a recombinant water-soluble collagen polypeptide comprising the steps of:

A) preparing and expressing a water-soluble collagen polypeptide in a yeast host cell culture containing yeast host cells using recombinant DNA technology, said culture comprising from about 10 to about 30 mmol of calcium ions, B) after centrifugation or diafiltration of said culture to remove said yeast host cells, isolating said expressed water-soluble collagen polypeptide from the supernatant by isoelectric precipitation at a pH which is within ±1 pH unit of the isoelectric point of said water-soluble collagen polypeptide, C) after centrifugation of the supernatant obtained in step B, resuspending the resulting pellet in a buffer, D) after centrifugation of the buffered solution formed in step C, subjecting the supernatant thereby obtained to ion exchange chromatography to capture said water-soluble collagen polypeptide, E) obtaining at least one elution fraction and subjecting it to either hydrophobic interaction chromatography or a second ion exchange chromatography, and F) recovering said water-soluble collagen polypeptide from at least one elution fraction obtained in step E, wherein between steps B and E, treating said water-soluble collagen polypeptide, independently, with a calcium salt and a protease, wherein said water-soluble collagen polypeptide comprises one of the following sequences:

Formula I:
$\{[(Gly\ Pro\ Gln)(Gly\ Pro\ Glu)_4]_2\}_n$
or
Formula II:
$Gly\ Pro\ Glu\{[(Gly\ Pro\ Gln)(Gly\ Pro\ Glu)_4]_2\}_n$
Formula III:
Gly Pro Xaa$_1$ Gly Leu Xaa$_2$ Gly Pro Arg Gly Pro Pro
Gly Ala Ser Gly Ala Pro Gly Pro Glu Gly Phe Gln Gly wherein Xaa$_1$ and Xaa$_2$ are independently the amino acids identified as Met, Ile, His, Lys, Asn, Tyr or Gln, and n is 1 to 25.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 93
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces cerevisiae ( v i i ) IMMEDIATE SOURCE: Saccharomyces cerevisiae ( x ) PUBLICATION INFORMATION: None ( x i ) SEQUENCE DESCRIPTION: SEQ ID NO:1:

```
Gly Pro Glu Gly Pro Gln Gly Pro Glu Gly Pro Glu
                  5                  10
Gly Pro Glu Gly Pro Glu Gly Pro Gln Gly Pro Glu
            15                  20
Gly Pro Glu Gly Pro Glu Gly Pro Glu Gly Pro Gln
25                  30                  35
Gly Pro Glu Gly Pro Glu Gly Pro Glu Gly Pro Glu
            40                  45
Gly Pro Gln Gly Pro Glu Gly Pro Glu Gly Pro Glu
      50                  55                  60
Gly Pro Glu Gly Pro Gln Gly Pro Glu Gly Pro Glu
                  65                  70
Gly Pro Glu Gly Pro Glu Gly Pro Gln Gly Pro Glu
            75                  80
Gly Pro Glu Gly Pro Glu Gly Pro Glu
85                  90
```

( 2 ) INFORMATION FOR SEQ ID NO:2:

( i ) SEQUENCE CHARACTERISTICS:
        ( A ) LENGTH: 123
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces cerevisiae ( v i i ) IMMEDIATE SOURCE: Saccharomyces cerevisiae ( x ) PUBLICATION INFORMATION: None ( x i ) SEQUENCE DESCRIPTION: SEQ ID NO:2:

```
Gly Pro Glu Gly Pro Gln Gly Pro Glu Gly Pro Glu
                  5                   10
Gly Pro Glu Gly Pro Glu Gly Pro Gln Gly Pro Glu
             15                  20
Gly Pro Glu Gly Pro Glu Gly Pro Glu Gly Pro Gln
25                      30                      35
Gly Pro Glu Gly Pro Glu Gly Pro Glu Gly Pro Glu
             40                  45
Gly Pro Gln Gly Pro Glu Gly Pro Glu Gly Pro Glu
     50                  55                      60
Gly Pro Glu Gly Pro Gln Gly Pro Glu Gly Pro Glu
                  65                  70
Gly Pro Glu Gly Pro Glu Gly Pro Gln Gly Pro Glu
             75                  80
Gly Pro Glu Gly Pro Glu Gly Pro Glu Gly Pro Gln
85                      90                      95
Gly Pro Glu Gly Pro Glu Gly Pro Glu Gly Pro Glu
             100                 105
Gly Pro Gln Gly Pro Glu Gly Pro Glu Gly Pro Glu
     110                 115                     120
Gly Pro Glu
```

( 2 ) INFORMATION FOR SEQ ID NO:3:

( i ) SEQUENCE CHARACTERISTICS:
    ( A ) LENGTH: 273
    ( B ) TYPE: Amino acid
    ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces cerevissiae ( v i i ) IMMEDIATE SOURCE: Saccharomyces cerevissiae ( x ) PUBLICATION INFORMATION: None ( x i ) SEQUENCE DESCRIPTION: SEQ ID NO:3:

```
Gly Pro Glu Gly Pro Gln Gly Pro Glu Gly Pro Glu
                  5                   10
Gly Pro Glu Gly Pro Glu Gly Pro Gln Gly Pro Glu
             15                  20
Gly Pro Glu Gly Pro Glu Gly Pro Glu Gly Pro Gln
25                      30                      35
Gly Pro Glu Gly Pro Glu Gly Pro Glu Gly Pro Glu
             40                  45
Gly Pro Gln Gly Pro Glu Gly Pro Glu Gly Pro Glu
     50                  55                      60
Gly Pro Glu Gly Pro Gln Gly Pro Glu Gly Pro Glu
                  65                  70
Gly Pro Glu Gly Pro Glu Gly Pro Gln Gly Pro Glu
```

```
                          75                        80
Gly  Pro  Glu  Gly  Pro  Glu  Gly  Pro  Glu  Gly  Pro  Gln
 85                      90                       95

Gly  Pro  Glu  Gly  Pro  Glu  Gly  Pro  Glu  Gly  Pro  Glu
               100                      105

Gly  Pro  Gln  Gly  Pro  Glu  Gly  Pro  Glu  Gly  Pro  Glu
          110                      115                     120

Gly  Pro  Glu  Gly  Pro  Gln  Gly  Pro  Glu  Gly  Pro  Glu
                    125                      130

Gly  Pro  Glu  Gly  Pro  Glu  Gly  Pro  Gln  Gly  Pro  Glu
          135                      140

Gly  Pro  Glu  Gly  Pro  Glu  Gly  Pro  Glu  Gly  Pro  Gln
145                      150                           155

Gly  Pro  Glu  Gly  Pro  Glu  Gly  Pro  Glu  Gly  Pro  Glu
               160                      165

Gly  Pro  Gln  Gly  Pro  Glu  Gly  Pro  Glu  Gly  Pro  Glu
          170                      175                     180

Gly  Pro  Glu  Gly  Pro  Gln  Gly  Pro  Glu  Gly  Pro  Glu
                    185                      190

Gly  Pro  Glu  Gly  Pro  Glu  Gly  Pro  Gln  Gly  Pro  Glu
          195                      200

Gly  Pro  Glu  Gly  Pro  Glu  Gly  Pro  Glu  Gly  Pro  Gln
205                      210                           215

Gly  Pro  Glu  Gly  Pro  Glu  Gly  Pro  Glu  Gly  Pro  Glu
               220                      225

Gly  Pro  Gln  Gly  Pro  Glu  Gly  Pro  Glu  Gly  Pro  Glu
          230                      235                     240

Gly  Pro  Glu  Gly  Pro  Gln  Gly  Pro  Glu  Gly  Pro  Glu
                    245                      250

Gly  Pro  Glu  Gly  Pro  Glu  Gly  Pro  Gln  Gly  Pro  Glu
          255                      260

Gly  Pro  Glu  Gly  Pro  Glu  Gly  Pro  Glu
265                      270
```

( 2 ) INFORMATION FOR SEQ ID NO:4:

( i ) SEQUENCE CHARACTERISTICS:
        ( A ) LENGTH: 30
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:4:

```
Gly  Pro  Gln  Gly  Pro  Glu  Gly  Pro  Glu  Gly  Pro  Glu
                     5                       10

Gly  Pro  Glu  Gly  Pro  Gln  Gly  Pro  Glu  Gly  Pro  Glu
          15                        20
```

Gly Pro Glu Gly Pro Glu
25                    30

( 2 ) INFORMATION FOR SEQ ID NO:5:

( i ) SEQUENCE CHARACTERISTICS:
        ( A ) LENGTH: 540
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces
            cerevisiae ( v i i ) IMMEDIATE SOURCE: Saccharomyces
              cerevisiae ( x ) PUBLICATION INFORMATION: None ( x i ) SEQUENCE DESCRIPTION: SEQ ID NO:5:

Gly Pro Gln Gly Pro Glu Gly Pro Glu Gly Pro Glu
                    5                   10

Gly Pro Glu Gly Pro Gln Gly Pro Glu Gly Pro Glu
            15                  20

Gly Pro Glu Gly Pro Glu Gly Pro Gln Gly Pro Glu
25                      30                  35

Gly Pro Glu Gly Pro Glu Gly Pro Glu Gly Pro Gln
            40                  45

Gly Pro Glu Gly Pro Glu Gly Pro Glu Gly Pro Glu
50                      55                      60

Gly Pro Gln Gly Pro Glu Gly Pro Glu Gly Pro Glu
            65                  70

Gly Pro Glu Gly Pro Gln Gly Pro Glu Gly Pro Glu
            75                  80

Gly Pro Glu Gly Pro Glu Gly Pro Gln Gly Pro Glu
85                      90                  95

Gly Pro Glu Gly Pro Glu Gly Pro Glu Gly Pro Gln
            100                 105

Gly Pro Glu Gly Pro Glu Gly Pro Glu Gly Pro Glu
            110                 115                 120

Gly Pro Gln Gly Pro Glu Gly Pro Glu Gly Pro Glu
                    125                 130

Gly Pro Glu Gly Pro Gln Gly Pro Glu Gly Pro Glu
            135                 140

Gly Pro Glu Gly Pro Glu Gly Pro Gln Gly Pro Glu
145                     150                 155

Gly Pro Glu Gly Pro Glu Gly Pro Glu Gly Pro Gln
            160                 165

Gly Pro Glu Gly Pro Glu Gly Pro Glu Gly Pro Glu
            170                 175                 180

Gly Pro Gln Gly Pro Glu Gly Pro Glu Gly Pro Glu
                    185                 190

Gly Pro Glu Gly Pro Gln Gly Pro Glu Gly Pro Glu
            195                 200

-continued

Gly Pro Glu Gly Pro Glu Gly Pro Gln Gly Pro Glu
205                    210                215

Gly Pro Glu Gly Pro Glu Gly Pro Glu Gly Pro Gln
            220                225

Gly Pro Glu Gly Pro Glu Gly Pro Glu Gly Pro Glu
230                    235                    240

Gly Pro Gln Gly Pro Glu Gly Pro Glu Gly Pro Glu
            245                250

Gly Pro Glu Gly Pro Gln Gly Pro Glu Gly Pro Glu
            255                260

Gly Pro Glu Gly Pro Glu Gly Pro Gln Gly Pro Glu
265                    270                275

Gly Pro Glu Gly Pro Glu Gly Pro Glu Gly Pro Gln
            280                285

Gly Pro Glu Gly Pro Glu Gly Pro Glu Gly Pro Glu
            290                295                    300

Gly Pro Gln Gly Pro Glu Gly Pro Glu Gly Pro Glu
            305                310

Gly Pro Glu Gly Pro Gln Gly Pro Glu Gly Pro Glu
            315                320

Gly Pro Glu Gly Pro Glu Gly Pro Gln Gly Pro Glu
325                    330                335

Gly Pro Glu Gly Pro Glu Gly Pro Glu Gly Pro Gln
            340                345

Gly Pro Glu Gly Pro Glu Gly Pro Glu Gly Pro Glu
350                    355                    360

Gly Pro Gln Gly Pro Glu Gly Pro Glu Gly Pro Glu
            365                370

Gly Pro Glu Gly Pro Gln Gly Pro Glu Gly Pro Glu
            375                380

Gly Pro Glu Gly Pro Glu Gly Pro Gln Gly Pro Glu
385                    390                395

Gly Pro Glu Gly Pro Glu Gly Pro Glu Gly Pro Glu
            400                405

Gly Pro Glu Gly Pro Glu Gly Pro Glu Gly Pro Glu
410                    415                    420

Gly Pro Gln Gly Pro Glu Gly Pro Glu Gly Pro Glu
            425                430

Gly Pro Glu Gly Pro Gln Gly Pro Glu Gly Pro Glu
            435                440

Gly Pro Glu Gly Pro Glu Gly Pro Gln Gly Pro Glu
445                    450                455

Gly Pro Glu Gly Pro Glu Gly Pro Glu Gly Pro Gln
            460                465

Gly Pro Glu Gly Pro Glu Gly Pro Glu Gly Pro Glu
470                    475                    480

Gly Pro Gln Gly Pro Glu Gly Pro Glu Gly Pro Glu
            485                490

Gly Pro Glu Gly Pro Gln Gly Pro Glu Gly Pro Glu
            495                500

Gly Pro Glu Gly Pro Glu Gly Pro Gln Gly Pro Glu
505                    510                515

Gly Pro Glu Gly Pro Glu Gly Pro Glu Gly Pro Gln

```
                        520                        525
Gly  Pro  Glu  Gly  Pro  Glu  Gly  Pro  Glu  Gly  Pro  Glu
        530                        535                       540
```

( 2 ) INFORMATION FOR SEQ ID NO:6:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:6:

```
Gly  Pro  Ile  Gly  Leu  Ile  Gly  Pro  Arg  Gly  Pro  Pro
                      5                        10
Gly  Ala  Ser  Gly  Ala  Pro  Gly  Pro  Glu  Gly  Phe  Gln
            15                        20
Gly
 25
```

( 2 ) INFORMATION FOR SEQ ID NO:7:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:7:

```
Gly  Pro  Lys  Gly  Leu  Lys  Gly  Pro  Arg  Gly  Pro  Pro
                      5                        10
Gly  Ala  Ser  Gly  Ala  Pro  Gly  Pro  Glu  Gly  Phe  Gln
            15                        20
Gly
 25
```

( 2 ) INFORMATION FOR SEQ ID NO:8:

( i ) SEQUENCE CHARACTERISTICS:
        ( A ) LENGTH: 25
        ( B ) TYPE: Amino acid
        ( D ) TOPOLOGY: Linear (ii) MOLECULE TYPE: Polypeptide (iii) HYPOTHETICAL: No (iv) ANTI-SENSE: No (v) FRAGMENT TYPE: Internal (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:8:

Gly Pro Asn Gly Leu Asn Gly Pro Arg Gly Pro Pro
                  5                   10
Gly Ala Ser Gly Ala Pro Gly Pro Glu Gly Phe Gln
         15                  20
Gly
 25

(2) INFORMATION FOR SEQ ID NO:9:

(i) SEQUENCE CHARACTERISTICS:
    (A) LENGTH: 25
    (B) TYPE: Amino acid
    (D) TOPOLOGY: Linear (ii) MOLECULE TYPE: Polypeptide (iii) HYPOTHETICAL: No (iv) ANTI-SENSE: No (v) FRAGMENT TYPE: Internal (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:9:

Gly Pro Tyr Gly Leu Tyr Gly Pro Arg Gly Pro Pro
                  5                   10
Gly Ala Ser Gly Ala Pro Gly Pro Glu Gly Phe Gln
         15                  20
Gly
 25

(2) INFORMATION FOR SEQ ID NO:10:

(i) SEQUENCE CHARACTERISTICS:
    (A) LENGTH: 25
    (B) TYPE: Amino acid
    (D) TOPOLOGY: Linear (ii) MOLECULE TYPE: Polypeptide (iii) HYPOTHETICAL: No (iv) ANTI-SENSE: No (v) FRAGMENT TYPE: Internal (vi) ORIGINAL SOURCE: Synthetically prepared (vii) IMMEDIATE SOURCE: Synthetically prepared ( x ) PUBLICATION INFORMATION: None ( x i ) SEQUENCE DESCRIPTION: SEQ ID NO:10:

Gly Pro Gln Gly Leu Gln Gly Pro Arg Gly Pro Pro
　　　　　　　　　5　　　　　　　　　　　　10
Gly Ala Ser Gly Ala Pro Gly Pro Glu Gly Phe Gln
　　　　　15　　　　　　　　　　20
Gly
25

( 2 ) INFORMATION FOR SEQ ID NO:11:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:11:

Gly Pro Met Gly Leu Met Gly Pro Arg Gly Pro Pro
　　　　　　　　　5　　　　　　　　　　　　10
Gly Ala Ser Gly Ala Pro Gly Pro Glu Gly Phe Gln
　　　　　15　　　　　　　　　　20
Gly
25

( 2 ) INFORMATION FOR SEQ ID NO:12:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:12:

Gly Pro His Gly Leu His Gly Pro Arg Gly Pro Pro
　　　　　　　　　5　　　　　　　　　　　　10
Gly Ala Ser Gly Ala Pro Gly Pro Glu Gly Phe Gln
　　　　　15　　　　　　　　　　20
Gly
25

( 2 ) INFORMATION FOR SEQ ID NO:13:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically
             prepared ( x ) PUBLICATION INFORMATION: None ( x i ) SEQUENCE DESCRIPTION: SEQ ID NO:13:

Gly Pro Ile Gly Leu Met Gly Pro Arg Gly Pro Pro
                  5                   10
Gly Ala Ser Gly Ala Pro Gly Pro Glu Gly Phe Gln
         15                  20
Gly
 25

( 2 ) INFORMATION FOR SEQ ID NO:14:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically
             prepared ( x ) PUBLICATION INFORMATION: None ( x i ) SEQUENCE DESCRIPTION: SEQ ID NO:14:

Gly Pro Met Gly Leu Ile Gly Pro Arg Gly Pro Pro
                  5                   10
Gly Ala Ser Gly Ala Pro Gly Pro Glu Gly Phe Gln
         15                  20
Gly
 25

( 2 ) INFORMATION FOR SEQ ID NO:15:

( i ) SEQUENCE CHARACTERISTICS:
        ( A ) LENGTH: 270
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Saccharomyces cerevisiae ( v i i ) IMMEDIATE SOURCE: Saccharomyces cerevisiae ( x ) PUBLICATION INFORMATION: None ( x i ) SEQUENCE DESCRIPTION: SEQ ID NO:15:

```
Gly Pro Gln Gly Pro Glu Gly Pro Glu Gly Pro Glu
                  5                  10
Gly Pro Glu Gly Pro Gln Gly Pro Glu Gly Pro Glu
            15                  20
Gly Pro Glu Gly Pro Glu Gly Pro Gln Gly Pro Glu
 25                  30                       35
Gly Pro Glu Gly Pro Glu Gly Pro Glu Gly Pro Gln
            40                  45
Gly Pro Glu Gly Pro Glu Gly Pro Glu Gly Pro Glu
 50                  55                       60
Gly Pro Gln Gly Pro Glu Gly Pro Glu Gly Pro Glu
                  65                  70
Gly Pro Glu Gly Pro Gln Gly Pro Glu Gly Pro Glu
            75                  80
Gly Pro Glu Gly Pro Glu Gly Pro Gln Gly Pro Glu
 85                  90                       95
Gly Pro Glu Gly Pro Glu Gly Pro Glu Gly Pro Gln
            100                 105
Gly Pro Glu Gly Pro Glu Gly Pro Glu Gly Pro Glu
 110                 115                      120
Gly Pro Gln Gly Pro Glu Gly Pro Glu Gly Pro Glu
                  125                 130
Gly Pro Glu Gly Pro Gln Gly Pro Glu Gly Pro Glu
            135                 140
Gly Pro Glu Gly Pro Glu Gly Pro Gln Gly Pro Glu
 145                 150                      155
Gly Pro Glu Gly Pro Glu Gly Pro Glu Gly Pro Gln
            160                 165
Gly Pro Glu Gly Pro Glu Gly Pro Glu Gly Pro Glu
 170                 175                      180
Gly Pro Gln Gly Pro Glu Gly Pro Glu Gly Pro Glu
                  185                 190
Gly Pro Glu Gly Pro Gln Gly Pro Glu Gly Pro Glu
            195                 200
Gly Pro Glu Gly Pro Glu Gly Pro Gln Gly Pro Glu
 205                 210                      215
Gly Pro Glu Gly Pro Glu Gly Pro Glu Gly Pro Gln
            220                 225
Gly Pro Glu Gly Pro Glu Gly Pro Glu Gly Pro Glu
 230                 235                      240
Gly Pro Gln Gly Pro Glu Gly Pro Glu Gly Pro Glu
                  245                 250
Gly Pro Glu Gly Pro Gln Gly Pro Glu Gly Pro Glu
            255                 260
```

Gly Pro Glu Gly Pro Glu
265                 270

( 2 ) INFORMATION FOR SEQ ID NO:16:

( i ) SEQUENCE CHARACTERISTICS:
       ( A ) LENGTH: 543
       ( B ) TYPE: Amino acid
       ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces
           cerevisiae ( v i i ) IMMEDIATE SOURCE: Saccharomyces
             cerevisiae ( x ) PUBLICATION INFORMATION: None ( x i ) SEQUENCE DESCRIPTION: SEQ ID NO:16:

Gly Pro Glu Gly Pro Gln Gly Pro Glu Gly Pro Glu
                    5                  10
Gly Pro Glu Gly Pro Glu Gly Pro Gln Gly Pro Glu
            15                 20
Gly Pro Glu Gly Pro Glu Gly Pro Glu Gly Pro Gln
25                      30                 35
Gly Pro Glu Gly Pro Glu Gly Pro Glu Gly Pro Glu
            40                 45
Gly Pro Gln Gly Pro Glu Gly Pro Glu Gly Pro Glu
        50              55                     60
Gly Pro Glu Gly Pro Gln Gly Pro Glu Gly Pro Glu
                65              70
Gly Pro Glu Gly Pro Glu Gly Pro Gln Gly Pro Glu
            75                 80
Gly Pro Glu Gly Pro Glu Gly Pro Glu Gly Pro Gln
85              90                      95
Gly Pro Glu Gly Pro Glu Gly Pro Glu Gly Pro Glu
                100                 105
Gly Pro Gln Gly Pro Glu Gly Pro Glu Gly Pro Glu
    110             115                     120
Gly Pro Glu Gly Pro Gln Gly Pro Glu Gly Pro Glu
                125                 130
Gly Pro Glu Gly Pro Glu Gly Pro Gln Gly Pro Glu
            135                 140
Gly Pro Glu Gly Pro Glu Gly Pro Glu Gly Pro Gln
145                 150                 155
Gly Pro Glu Gly Pro Glu Gly Pro Glu Gly Pro Glu
                160                 165
Gly Pro Gln Gly Pro Glu Gly Pro Glu Gly Pro Glu
    170                 175                     180
Gly Pro Glu Gly Pro Gln Gly Pro Glu Gly Pro Glu
                185                 190
Gly Pro Glu Gly Pro Glu Gly Pro Gln Gly Pro Glu
            195                 200

```
Gly Pro Glu Gly Pro Glu Gly Pro Glu Gly Pro Gln
205                 210                 215
Gly Pro Glu Gly Pro Glu Gly Pro Glu Gly Pro Glu
                220                 225
Gly Pro Gln Gly Pro Glu Gly Pro Glu Gly Pro Glu
        230                 235                 240
Gly Pro Glu Gly Pro Gln Gly Pro Glu Gly Pro Glu
                245                 250
Gly Pro Glu Gly Pro Glu Gly Pro Gln Gly Pro Glu
            255                 260
Gly Pro Glu Gly Pro Glu Gly Pro Glu Gly Pro Gln
265                 270                 275
Gly Pro Glu Gly Pro Glu Gly Pro Glu Gly Pro Glu
                280                 285
Gly Pro Gln Gly Pro Glu Gly Pro Glu Gly Pro Glu
        290                 295                 300
Gly Pro Glu Gly Pro Gln Gly Pro Glu Gly Pro Glu
                305                 310
Gly Pro Glu Gly Pro Glu Gly Pro Gln Gly Pro Glu
            315                 320
Gly Pro Glu Gly Pro Glu Gly Pro Glu Gly Pro Gln
325                 330                 335
Gly Pro Glu Gly Pro Glu Gly Pro Glu Gly Pro Glu
                340                 345
Gly Pro Gln Gly Pro Glu Gly Pro Glu Gly Pro Glu
        350                 355                 360
Gly Pro Glu Gly Pro Glu Gly Pro Gln Gly Pro Glu
                365                 370
Gly Pro Glu Gly Pro Glu Gly Pro Gln Gly Pro Glu
            375                 380
Gly Pro Glu Gly Pro Glu Gly Pro Glu Gly Pro Gln
385                 390                 395
Gly Pro Glu Gly Pro Glu Gly Pro Glu Gly Pro Glu
                400                 405
Gly Pro Gln Gly Pro Glu Gly Pro Glu Gly Pro Glu
        410                 415                 420
Gly Pro Glu Gly Pro Gln Gly Pro Glu Gly Pro Glu
                425                 430
Gly Pro Glu Gly Pro Glu Gly Pro Gln Gly Pro Glu
            435                 440
Gly Pro Glu Gly Pro Glu Gly Pro Glu Gly Pro Gln
445                 450                 455
Gly Pro Glu Gly Pro Glu Gly Pro Glu Gly Pro Glu
                460                 465
Gly Pro Gln Gly Pro Glu Gly Pro Glu Gly Pro Glu
        470                 475                 480
Gly Pro Glu Gly Pro Gln Gly Pro Glu Gly Pro Glu
                485                 490
Gly Pro Glu Gly Pro Glu Gly Pro Gln Gly Pro Glu
            495                 500
Gly Pro Glu Gly Pro Glu Gly Pro Glu Gly Pro Gln
505                 510                 515
Gly Pro Glu Gly Pro Glu Gly Pro Glu Gly Pro Glu
                520                 525
```

Gly Pro Gln Gly Pro Glu Gly Pro Glu Gly Pro Glu
530                  535                 540

Gly Pro Glu ( 2 ) INFORMATION FOR SEQ ID NO:17:

( i ) SEQUENCE CHARACTERISTICS:
        ( A ) LENGTH: 109 nucleotides
        ( B ) TYPE: Nucleic acid
        ( C ) STRANDEDNESS: Single
        ( D ) TOPOLOGY: Linear ( i i ) MOLECULE TYPE: Encoding DNA strand ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:17:

```
AATTCGGTCC CGAGGGTCCA CAAGGTCCAG AAGGTCCAGA          40

AGGTCCAGAA GGTCCAGAAG GTCCACAAGG TCCAGAAGGT          80

CCAGAAGGTC CAGAAGGTCC CGAGCTAAG                     109
```

( 2 ) INFORMATION FOR SEQ ID NO:18:

( i ) SEQUENCE CHARACTERISTICS:
        ( A ) LENGTH: 109 nucleotides
        ( B ) TYPE: Nucleic acid
        ( C ) STRANDEDNESS: Single
        ( D ) TOPOLOGY: Linear ( i i ) MOLECULE TYPE: Encoding DNA strand ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:18:

```
TCGACTTAGC TCGGGACCTT CTGGACCTTC TGGACCTTCT          40

GGACCTTGTG GACCTTCTGG ACCTTCTGGA CCTTCTGGAC          80

CTTCTGGACC TTGTGGACCC TCGGGACCG                     109
```

( 2 ) INFORMATION FOR SEQ ID NO:19:

( i ) SEQUENCE CHARACTERISTICS:
        ( A ) LENGTH: 105
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No (v) FRAGMENT TYPE: C-terminal (vi) ORIGINAL SOURCE: Saccharomyces cerevisiae (vii) IMMEDIATE SOURCE: Saccharomyces cerevisiae (x) PUBLICATION INFORMATION: None (xi) SEQUENCE DESCRIPTION: SEQ ID NO:19:

```
Asp Tyr Lys Asp Asp Asp Asp Lys Glu Phe Gly Lys
                 5                   10
Gly Pro Glu Gly Pro Gln Gly Pro Glu
             15              20
Gly Pro Glu Gly Pro Glu Gly Pro Glu Gly Pro Gln
             25                  30
Gly Pro Glu Gly Pro Glu Gly Pro Glu Gly Pro Glu
             35              40              45
Gly Pro Gln Gly Pro Glu Gly Pro Glu Gly Pro Glu
                 50                  55
Gly Pro Glu Gly Pro Gln Gly Pro Glu Gly Pro Glu
             60                  65
Gly Pro Glu Gly Pro Glu Gly Pro Gln Gly Pro Glu
70                       75                  80
Gly Pro Glu Gly Pro Glu Gly Pro Glu Gly Pro Gln
             85                  90
Gly Pro Glu Gly Pro Glu Gly Pro Glu Gly Pro Glu
             95          100             105
```

(2) INFORMATION FOR SEQ ID NO:20:

(i) SEQUENCE CHARACTERISTICS:
  (A) LENGTH: 285
  (B) TYPE: Amino acid
  (D) TOPOLOGY: Linear (ii) MOLECULE TYPE: Polypeptide (iii) HYPOTHETICAL: No (iv) ANTI-SENSE: No (v) FRAGMENT TYPE: C-terminal (vi) ORIGINAL SOURCE: Saccharomyces cerevisiae (vii) IMMEDIATE SOURCE: Saccharomyces cerevisiae (x) PUBLICATION INFORMATION: None (xi) SEQUENCE DESCRIPTION: SEQ ID NO:20:

```
Asp Tyr Lys Asp Asp Asp Asp Lys Glu Phe Gly Lys
                 5                   10
Gly Pro Glu Gly Pro Gln Gly Pro Glu Gly Pro Glu
             15                  20
Gly Pro Glu Gly Pro Glu Gly Pro Gln Gly Pro Glu
25                       30                  35
Gly Pro Glu Gly Pro Glu Gly Pro Glu Gly Pro Gln
             40                  45
Gly Pro Glu Gly Pro Glu Gly Pro Glu Gly Pro Glu
             50                  55                  60
```

-continued

```
Gly Pro Gln Gly Pro     Glu Gly Pro Glu Gly Pro     Glu
                65                       70
Gly Pro Glu Gly Pro     Gln Gly Pro     Glu Gly Pro Glu
        75                      80
Gly Pro Glu Gly Pro Glu Gly Pro Gln Gly Pro     Glu
85                  90                      95
Gly Pro Glu Gly     Pro Glu Gly Pro Glu Gly Pro Gln
            100             105
Gly Pro Glu Gly Pro Glu Gly     Pro Glu Gly Pro     Glu
        110             115                     120
Gly Pro Gln Gly Pro     Glu Gly Pro Glu Gly     Pro Glu
                125                     130
Gly Pro Glu Gly Pro Gln Gly Pro     Glu Gly Pro Glu
        135                     140
Gly Pro Glu Gly Pro     Glu Gly Pro Gln Gly Pro     Glu
145                 150                     155
Gly Pro Glu Gly Pro     Glu Gly Pro Glu Gly Pro Gln
                160                     165
Gly Pro Glu Gly Pro     Glu Gly Pro     Glu Gly Pro     Glu
        170                     175                     180
Gly Pro Gln Gly Pro     Glu Gly Pro Glu Gly Pro     Glu
                185                             190
Gly Pro Glu Gly Pro Gln Gly Pro     Glu Gly Pro Glu
            195                 200
Gly Pro Glu Gly Pro     Glu Gly Pro Gln Gly Pro     Glu
205                 210                     215
Gly Pro Glu Gly     Pro Glu Gly Pro Glu Gly Pro Gln
            220                     225
Gly Pro Glu Gly Pro Glu Gly     Pro Glu Gly Pro     Glu
        230             235                     240
Gly Pro Gln Gly Pro     Glu Gly Pro Glu Gly Pro     Glu
                245                     250
Gly Pro Glu Gly Pro Gln Gly Pro     Glu Gly Pro Glu
            255                 260
Gly Pro Glu Gly Pro     Glu Gly Pro Gln Gly Pro     Glu
265                 270                     275
Gly Pro Glu Gly     Pro Glu Gly Pro Glu
            280                     285
```